(12) United States Patent
Deneris et al.

(10) Patent No.: US 6,384,204 B1
(45) Date of Patent: May 7, 2002

(54) REAGENTS AND METHODS FOR THE SCREENING OF COMPOUNDS USEFUL IN THE TREATMENT OF NEUROLOGICAL DISEASES

(76) Inventors: Evan Samuel Deneris, 2591 Kerwick Rd., University Heights, OH (US) 44118; Dmitry Viktor Fyodorov, 4317 Clairemont Dr., San Diego, CA (US) 92117; Timothy John Hendricks, 2777 Lancashire Rd., Apt. 2, Cleveland Heights, OH (US) 44106

(*) Notice: Subject to any disclaimer, the term of this patent is extended or adjusted under 35 U.S.C. 154(b) by 0 days.

(21) Appl. No.: 09/435,335

(22) Filed: Nov. 5, 1999

Related U.S. Application Data

(63) Continuation-in-part of application No. 09/360,779, filed on Jul. 26, 1999.
(60) Provisional application No. 60/094,264, filed on Jul. 27, 1998.

(51) Int. Cl.[7] .................. C07H 21/04; C07H 21/02; C07H 19/00; C07K 14/00
(52) U.S. Cl. ................ 536/23.5; 536/23.1; 536/22.1; 530/350; 435/71.1
(58) Field of Search ............. 435/69.1, 326.1, 435/71.1, 193, 243; 536/23.1, 22.1, 23.5; 530/350

(56) References Cited

U.S. PATENT DOCUMENTS 5,521,300 A * 5/1996 Shah et al. ............. 536/24.32
5,605,821 A * 2/1997 McEver et al. .......... 435/172.3
6,110,666 A * 8/2000 Grosveld et al. ............ 435/6

FOREIGN PATENT DOCUMENTS

EP           592894 A1 * 4/1994 ............ C12Q/1/68

* cited by examiner

Primary Examiner—Karen Cochrane Carlson
Assistant Examiner—Rita Mitra
(74) Attorney, Agent, or Firm—Medlen & Carroll, PLC LLP

(57) ABSTRACT

This invention relates to the gene sequence of a novel transcription factor specific for central 5-HT (serotonergic) neurons. The sequence and products are useful in screening methods for identifying and testing agonists and antagonists of seronergic activity.

2 Claims, 13 Drawing Sheets

(2 of 13 Drawing Sheet(s) Filed in Color)

```
tttgttttaacaaacatgtttattagaaaagtaaaaatattgcataggtcttagtacttgaacatcaagtgtatt  75
catgaaccgtgagtatcttcatgtaaacagttctagATGGAAGACCCAGGTGGCGCTCCTCTGGGGGAGAGGGTT  150
                                   *  M  E  D  P  G  G  A  P  L  G  E  R  V   13

CCAGCCCCCACCCCCCTCAGCCCCATCCCCTCACAGCTCACTCCTCCAGTACACCGGCACCGGGATGGGCTGGG  225
 P  A  P  H  P  P  Q  P  H  P  L  T  A  H  S  S  S  T  P  A  P  G  W  A  G   38

ATGCAGCTCCAGGACCCCCTCCCTCCTCACCACACCCTGGCTGCCCGCTCCCGCCAGGCCTTGCCGGACCCGGCG  300
 M  Q  L  Q  D  P  L  P  P  H  H  T  L  A  A  R  S  R  Q  A  L  P  D  P  A   63

GCGTCTACTCTTCCCTGTCACCCACAGTCACCACGGGCGGGTATCGGCACCCCAAGCGCAAAGCTGACGTGCCCC  375
 A  S  T  L  P  C  H  P  Q  S  P  R  A  G  I  G  T  P  S  A  K  L  T  C  P   88

CCCGTGCGGTCCCCCCCATCTCCCACCGCCCAGTCCCCGGCAGCGATGAGACAGAGCGGCACCTCCCAGCCCCTG  450
 P  V  R  S  P  P  S  P  T  A  Q  S  P  A  A  M  R  Q  S  G  T  S  Q  P  L   113

CTGATCAACATGTACCTACCAGATCCCGTCGGAGATGGTCTTTTTAAGGAAGGGAAGAGCCCGAGCTGGGGCCG  525
 L  I  N  M  Y  L  P  D  P  V  G  D  G  L  F  K  E  G  K  S  P  S  W  G  P   138

CTGAGCCCTGCGGTACAGAAAGGCAGCGGGCAGATCCAGTTGTGGCAGTTTCTACTGGAGCTGCTGGCAGACCGC  600
 L  S  P  A  V  Q  K  G  S  G  Q  I  Q  L  W  Q  F  L  L  E  L  L  A  D  R   163

GCGAACGCCGGCTGCATCGCGTGGGAGGGCGGCCACGGCGAGTTCAAGCTCACCGACCCCGACGAGGTGGCGCGA  675
 A  N  A  G  C  I  A  W  E  G  G  H  G  E  F  K  L  T  D  P  D  E  V  A  R   188

CGCTGGGGCGAGCGCAAGAGCAAGCCCAATATGAACTACGACAAGCTAAGTCGAGCACTGCGCTACTACTACGAC  750
 R  W  G  E  R  K  S  K  P  N  M  N  Y  D  K  L  S  R  A  L  R  Y  Y  Y  D   213

AAAAACATCATGAGCAAGGTGCACGGCAAGCGCTACGCCTACCGCTTTGACTTCCAGGGCCTGGCACAGGCTTGC  825
 K  N  I  M  S  K  V  H  G  K  R  Y  A  Y  R  F  D  F  Q  G  L  A  Q  A  C   238

CAGCCACCACCCGCGCACGCCCACGCCGCCGCTGCCGCCGCCGCAGCGGCAGCCGCCGCCCAGGATGGCGCACTT  900
 Q  P  P  P  A  H  A  H  A  A  A  A  A  A  A  A  A  A  Q  D  G  A  L   263

TACAAGCTCCCGGCTGGTCTGGCTCCACTGCCCTTCCCCGGCCTCTCCAAACTCAACCTTATGGCAGCCTCGGCC  975
 Y  K  L  P  A  G  L  A  P  L  P  F  P  G  L  S  K  L  N  L  M  A  A  S  A   288

GGCGTGGCGCCCGCTGGCTTCTCTTACTGGCCTGGTCCCAACGCCACCGCCGCTGCCGCCGCCACCGCTGCGCTC  1050
 G  V  A  P  A  G  F  S  Y  W  P  G  P  N  A  T  A  A  A  A  T  A  A  L   313

TACCCAACCCCGGGCTTGCAGCCCCCTCCCGGGCCCTTTGGCGCGGTGGCCGCCGCTTCGCACTTGGGGGGTCAT  1125
 Y  P  T  P  G  L  Q  P  P  P  G  P  F  G  A  V  A  A  A  S  H  L  G  G  H   338

TATCACtagacgggacggccgggtgcagtggggcctctcccacacagccagtgaccaatccatcctcatcctgg  1200
 Y  H  *
gaggagccccgaagatttccccgacgttcctttaccacagatttcgttgcagcagccgctcccagcccagggaag  1275
aaaggatgggaagcctctgaggtcttccttgaatacgaggcttccaggctcccattatcatcacccagggaaggg  1350
tgcatgtgctcccactttaatttttctcttccaagtctccagattctggaactcccgtctttttttctcttctc  1425
acctggagccctgccttcctctttatgaccctagttttctgttttgtttttttttttcctctctctctcctc  1500
attttttttctctcccacgacctactccaaacggtagtacctcggtagtacctcgaggcttctcacactcccctt  1575
ttcgggatatgagaagcatcaaaaacatctctgctgttgtccatccctatcccaacactctggcttcgctccctt  1650
ccataccacactctggcccaaggaccctcgtctgtatatattcctttcagccccATTAAAgatccaagcttcaaa  1725
aaaaaaaaaaaaaaaaaaaaaaaaaa
```

REAGENTS AND METHODS FOR THE SCREENING OF COMPOUNDS USEFUL IN THE TREATMENT OF NEUROLOGICAL DISEASES

This application for patent under 35 U.S.C. 111(a) claims priority to Provisional Application Ser. No. 60/094,264 filed Jul. 27, 1998 under 35 U.S.C. 111(b).

The present application is a continuation-in-part of application Ser. No. 09/360,779 filed Jul. 26, 1999.

This invention was supported in part by grants form the National Institutes of Health; numbers RO1-NS29123 and NIH NIMH MH58926.

FIELD OF INVENTION

This invention relates to a novel DNA sequence, and derivatives thereof, useful in the screening of compounds that are agonistic or antagonistic to seronergic receptor activity.

BACKGROUND

The enormous phenotypic diversity of neural cell types implies a corresponding complexity of gene-specific transcription factor combinations required to regulate thousands of genes in the appropriate stage and cell type-specific manner (He, X., and Rosenfeld, M. G., "Mechanisms of complex transcriptional regulation: implications for brain development" *Neuron* 7:183–196, 1991; Mandel, G., and McKinnon, D, "Molecular basis of neural-specific gene expression" *Annu. Rev. Neurosci.* 16:323–345, 1993; Struhl, K., "Mechanisms for diversity in gene expression patterns" *Neuron* 7:177–181, 1991). Indeed, several members of different transcription factor classes, such as homeodomain, zinc-finger and basic helix-loop-helix proteins, function to regulate neural cell-type identity in specific regions of both the vertebrate and invertebrate nervous systems. Many of these genes are expressed early in neural development, which suggests they play a critical role in neurogenesis and neuronal patterning (Tanabe, Y., and Jessell, T. M., "Diversity and pattern in the developing spinal cord" *Science* 274:1115–1124, 1996). However, an understanding of the functional interplay between different transcription factors and the neural genes they regulate is just beginning to emerge. Little ia known about the identity and specific functions of transcription factors which operate particular differentiation programs involved in the appearance and maintenance of specific neural cell phenotypes.

The central serotonin (5-HT) neurotransmitter system consists of a relatively small population of morphologically diverse neurons whose cell bodies are present largely within the limits of the midbrain/hindbrain raphe nuclei and particular regions of the reticular formation (Steinbusch, H. W. M., *Neuroscience* 6:557–618, 1981). Although there are only about 20,000 serotonergic neurons in the rat brain the extensive axonal projection system arising from these neurons bears a tremendous number of collateral branches so that the 5-HT system densely innervates nearly all regions of the central nervous system (Halliday, G., Harding, A., and Paxinos, G. (1995) in *The rat nervous system* (Paxinos, G. ed), 2nd Ed., pp. 929–974, Academic Press, San Diego; Jacobs, B. L., and Azmitia, E. C., *Physiological Reviews* 72:165–220, 1992). Given its widespread distribution it is not surprising that 5-HT has been implicated in the control of numerous neural systems which mediate such functions as cognition, aggression, and perception (Heninger, G. R., *Proc. Natl. Acad. Sci. USA* 94:4823–4824, 1997). Abnormal function of the central 5-HT system has been implicated in several psychiatric maladies such as depression, anxiety, and eating disorders. The people afflicted by diseases caused or potentiated by abnormalities in the central serotonin 5-HT neurotransmitter system numbers in the millions. In this regard, this system is the target of several highly effective pharmacological agents that are used widely to treat these conditions. However, the current pharmacological agents may posses cross reactivity with other components of the central nervous system resulting in unwanted or debilitating side effects. Additionally, despite the clear importance of the central serotonin 5-HT system in a wide range of CNS processes and clinical disorders little is known about the genetic mechanisms which control the specification and differentiation of serotonergic neurons.

What is needed are reagents and methods that can be utilized in the screening of pharmacological compounds that can be utilized in the treatment of neurological diseases involving the central serotonin (5-HT) neurotransmitter system.

SUMMARY OF THE INVENTION

The present invention generally relates to compositions and methods of identifying and testing seronegic receptor agonists and antagonists. In addition, the invention relates to methods to identify other members of the EST transcription factor family, methods to identify homologs of Pet-1 which are native to other tissue or cell types or specific transcription factors for other neuronal cell types and methods to generate reagents derived from the invention.

The present invention contemplates employing a gene sequence (SEQ ID NO:1) that encodes a transcription factor specific for central serotonin 5-HT neurons. In one embodiment, the present invention contemplates a composition comprising isolated and purified DNA having an oligonucleotide sequence of: Pet-1 cDNA having the nucleotide sequence of SEQ ID NO:1. Such DNA may readily be inserted into expression constructs and the present invention contemplates such constructs as well as their use. The present invention also contemplates RNA transcribed from the above-indicated cDNA as well as protein (typically purified protein) translated from this RNA. Moreover, the present invention contemplates antibodies produced from immunizing with this translated protein.

The present invention also contemplates transgenic animals comprising the above-indicated DNA (i.e. the "transgene") or portions thereof. In a particular embodiment, the transgenic animal of the present invention may be generated with the transgene contained in an inducible, tissue specific promotor.

The present invention also contemplates using the above-named compositions in screening assays. The present invention is not limited by the particular method of screening. In one embodiment cells are used such as, but not limited to, transformed cell lines. In another embodiment primary cells may be used. The present invention is not limited to the nature of the transfection construct. The transfection constructs utilized will be the optimal constructs available for the cell line chosen at the time of setting up the assay. In one embodiment, the present invention contemplates screening suspected compounds in a system utilizing transfected cell lines. In one embodiment, the cells may be transfected transiently. In another embodiment, the cells may be stably transfected. In yet another embodiment translation products of the invention may be used in a cell-free assay system. In yet another embodiment, antibodies generated to the translation products of the invention may be used in immunoprecipitation assays.

The present invention may also be used to screen for Pet-1 binding sites in genomic DNA. In, one embodiment cDNA encoding the invention may be used in microchip assays. The present invention contemplates a method of screening, comprising: a) providing in any order: i) a first solid support (e.g. microchip) comprising DNA from a DNA library of the species to be examined and ii) a peptide, or portion thereof, encoded by the DNA of SEQ ID NO:1; b) contacting said microassay microchips with said peptide under conditions such that hybridization can take place.

The present invention may also be used to identify new transcription factors that function in central serotonin 5-HT neurons. In one embodiment, antibodies generated to translation products of the invention may be used in immunoprecipitation experiments to isolate novel transcription factors that interact with Pet-1. In another embodiment, the invention may be used to generate fusion proteins that could also be used to isolate novel transcription factors or other interactive proteins. In yet another embodiment, screens may be conducted using the yeast two-hybrid system.

The present invention may also be used to identify new homologs of Pet-1 or natural mutations thereof. The present invention contemplates screening for homologs using standard molecular procedures. In one embodiment screens are conducted using Northern and Southern blotting.

The present invention contemplates a method of screening a compound, said method comprising: a) providing in any order: i) a first group of cells comprising a recombinant expression vector, wherein said vector comprises at least a portion of the oligonueleotide sequence of SEQ ID NO:1, ii) a second group of cells comprising a recombinant expression vector, wherein said vector comprises a suitable control (i.e. an empty vector), and iii) at least one compound suspected of having the ability to modulate central serotonin 5-HT neuron activity; b) contacting said first and second groups of cells with said compound; and c) detecting the effects of said compound by screening for seronergic receptor generation or serotonin release by methods know to those practiced in the art.

The present invention also contemplates a method of screening for homologs, said method comprising: a) providing in any order: i) a nucleic acid comprising at least a portion of the sequence of SEQ ID NO: 1, and ii) DNA libraries from cells or tissues suspected to comprise said homolog; and b) hybridizing said first or second nucleic acid with said DNA of said library under conditions such that said DNA suspected of coding for said homolog is detected.

The present invention also contemplates a method of screening for interactive peptides, said method comprising: a) providing in any order: i) a peptide comprising at least a portion of the peptide sequence of SEQ ID NO: 2 (including but not limited to portions that are part of fusion proteins, i.e. proteins that contain another portion, such as a portion useful for protein purification) and b) an extract from source (e.g. cells or tissues) suspected of having said interactive peptides; and c) mixing said peptide with said extract under conditions such that said interactive peptide is detected.

The present invention contemplates another approach for screening for interactive peptides, said method comprising: a) providing in any order: i) antibodies reactive with (and usually specific for) at least a portion of a peptide having the sequence of SEQ ID NO: 2, and ii) an extract from a source (e.g. cells or tissues) suspected of having said interactive peptide(s); and b) mixing said antibody with said extract under conditions such that said interactive peptide is detected.

The present invention contemplates the generation of cell lines that express the Pet-1 gene, or portion thereof. The present invention is not limited to any particular cell line. Neuronal cells may be used. Likewise, non-neuronal cells may be used to establish a cell line that Pet-1 expression can be studied without interference of neuronal processes.

The present invention contemplates DNA binding assays where a) Pet-1 DNA (SEQ ID NO:1), or portion thereof, is either i) adhered to a solid support surface or ii) placed in a suspension, b) compounds suspected of binding to the DNA are added in a manner that promotes binding and c) binding is measured by methods known to those practiced in the art. Detection methods utilized may be, but are not limited to, staining, gel electrophoresis and spectrophometric methods.

The present invention contemplates high through put screening methods. Such methods may include, but are not limited to, DNA array assays, spectrophotometric assays, the use of robotics, the use of computerized assay systems and the use of commercially available systems.

The present invention contemplates screening for proteins that bind to Pet-1 binding sites selected from the group comprising SEQ ID NOS: 3, 4, 5, 6, 7, 8, 9, 10, 11 or 12 (Table 1). The present invention is not limited to any particular assay method. In one embodiment, DNA encoding these sequences is attached to a solid surface (i.e. a microchip) and protein suspected of binding the DNS sequences is placed in contact with the DNA. Attached proteins are then analysed by methods know to those in the art.

DEFINITIONS

To facilitate understanding of the invention, a number of terms are defined below.

As used herein "agent", "compound" or "drug" is used herein to denote a compound or mixture of chemical compounds, a biological macromolecule, or an extract made from biological materials such as bacteria, plants, fungi, or animal (particularly mammalian) cells or tissues that are suspected of having therapeutic properties. The compound, agent or drug may be purified, substantially purified or partially purified.

As used herein "agonist" refers to molecules or compounds which mimic the action of a "native" or "natural" compound. Agonists may or may not be homologous to these natural compounds in respect to conformation, charge or other characteristics. Thus, agonists may or may not be recognized by, e.g., receptors expressed on cell surfaces. In any event, regardless if the agonist is recognized by a natural compound in a manner similar to a "natural" compound or molecule, the agonist may cause physiologic and/or biochemical changes within the cell, such that the cell reacts to the presence of the agonist in the same manner as if the natural compound was present.

As used herein "antagonist" refers to molecules or compounds which inhibit the action of a "native" or "natural" compound. Antagonists may or may not be homologous to these natural compounds in respect to conformation, charge or other characteristics. Thus, antagonists may be recognized by the same or different receptors or molecules that are recognized by an agonist. Antagonists may have allosteric effects which prevent the action of an agonist (e.g., by modifying a DNA adduct, or antagonists may prevent the function of the agonist (e.g., by blocking a DNA repair molecule).

As used herein, the term "purified" or "to purify" refers to the removal of some contaminants from a sample. The present invention contemplates purified compositions (discussed above).

As used herein, the term "partially purified" refers to the removal of a moderate portion of the contaminants of a sample to the extent that the substance of interest is recognizable by techniques known to those skilled in the art as accounting for a measurable amount of the mixture.

As used herein, the term "substantially purified" refers to the removal of a significant portion of the contaminants of a sample (e.g. >90%) to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e. a region having affinity for another molecule) and such binding can take place (i.e. the binding region functions, albeit with perhaps lower affinity than that observed for the full-length protein). Such "functional portions" of the gene product are typically greater than 10 amino acids in length, and more typically greater than 50 amino acids in length, and even more typically greater than 100 amino acids in length. "Functional portions" may also be "conserved portions" of the protein. The alignment of the various gene products permit one skilled in the art to select conserved portions of the protein (i.e. those portions in common between two or more species) as well as unconserved portions (i.e. those portions unique to two or more species). The present invention contemplates conserved portions 10 amino acids in length or greater, and more typically greater than 50 amino acids in length.

The present invention contemplates the Pet-1 gene in operable combination with a promoter. "In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Patient" shall be defined as a human or other animal, such as a guinea pig or mouse and the like, capable of having cell cycle (influenced) determined diseases, either naturally occurring or induced, including but not limited to cancer.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression construct", "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "hybridization" as used herein refers to any process by which a strand of nucleic acid joins with a complementary strand through base pairing.

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4.H_2O$ and 1.85 g/l EDTA, pH adjusted to 7.4 with NaOH), 0.1% SDS, 5X Denhardt's reagent [50X Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4.H_2O$ and 1.85 g/l EDTA, pH adjusted to 7.4 with NaOH), 0.5% SDS, 5X Denhardt's reagent and 100 µg/ml denatured salmon sperm DNA followed by washing in a solution comprising 0.1X SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., Pet-1 and fragments thereof) joined to an exogenous protein fragment (the fusion partner which consists of a non-Pet-1 sequence). The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

"Antibody" shall be defined as a glycoprotein produced by B cells that binds with high specificity to the agent (usually, but not always, a peptide), or a structurally similar agent, that generated its production. Antibodies may be produced by any of the known methodologies (reference) and may be either polyclonal or monoclonal.

The phrase "gain-of-function" (gof) as used herein is applicable to the situation where a modified oligonucleotide that, when transfected into a host organism and translated into a peptide, results in a peptide that will function with increased efficiency (e.g. rate of reaction, affinity, etc.) as compared to the wild type peptide. For example, the modified oligonucleotide (or "gof nucleotide") may, in effect, function as an augmenter of the natural gene if the natural gene is present and functional in the host into which the gof oligonucleotide was transfected, or it may add that function to the host if the natural gene is not present or is non-functional.

The phrase "loss-of-function" (lof) as used herein is applicable to the situation where a modified oligonucleotide, when transfected into a host organism and translated into a peptide, results in a peptide that function with decreased efficiency (e.g. rate of reaction, affinity, etc.) as compared to the wild type peptide. For example, the modified oligonucleotide (or "lof" oligonucleotide") may, in effect, function as a diminisher of natural gene function if the natural gene is present and functional in the host into which the lof oligonucleotide was transfected, or may negatively interfere with processes in the host if the natural gene is not present or is non-functional.

DESCRIPTION OF FIGURES

The file of this patent contains at least one drawing executed in color. Copies of this patent with color drawing (s) will be provided by the Patent and Trademark Office upon request and payment of necessary fees.

FIG. 1 shows the nucleotide sequence (SEQ ID NO:1) of the λ73 cDNA and the deduced primary structure of Pet-1 (SEQ ID NO:2). The two sets of numbering on the right mark either the nucleotide sequence or amino acid residue. Translation termination codons flanking the open reading frame are marked by asterisks. The ETS domain is contained within the dashed lines. Underlined amino-acid sequences within the ETS domain mark homologous region in other ETS-domains that were used to prepare primers for the degenerate PCR screen. Boxed residues indicate putative MAP kinase phosphorylation sites. A putative nucleotide binding P-loop is enclosed by an oval. A possible polyadenylation signal motif is shown in capital letters at the end of the nucleotide sequence.

FIG. 5 shows that Pet-1 can bind DNA in an ETS-binding site dependent manner. In vitro translated EE-tagged Pet-1 protein was used for an EMSA experiment along with 0.1 pmoles radiolabeled double-stranded oligonucleotide bearing a single PEA3 ETS DNA binding motif. Lanes 1, probe alone; lane 2, no EE-Pet-1 template; lanes 3–8, in vitro translation reactions programmed with EE-Pet-1 template; lane 3, no competitor; lane 4, 2 pmoles wild-type unlabeled PEA3 oligonucleotide added as a competitor; lane 5, 10 pmoles unlabeled PEA3 oligonucleotide; lane 6, 2 pmoles mutated PEA3 oligonucleotide; lane 7, 10 pmoles mutated PEA3 oligonucleotide; lane 8, 1 $\mu$g monoclonal EE-tag specific antibody. The bottom arrow indicates the position of the free probe, middle arrow indicates the specific protein-DNA complex, and top arrow indicates supershifted complex obtained with EE antibody.

Figure 6:
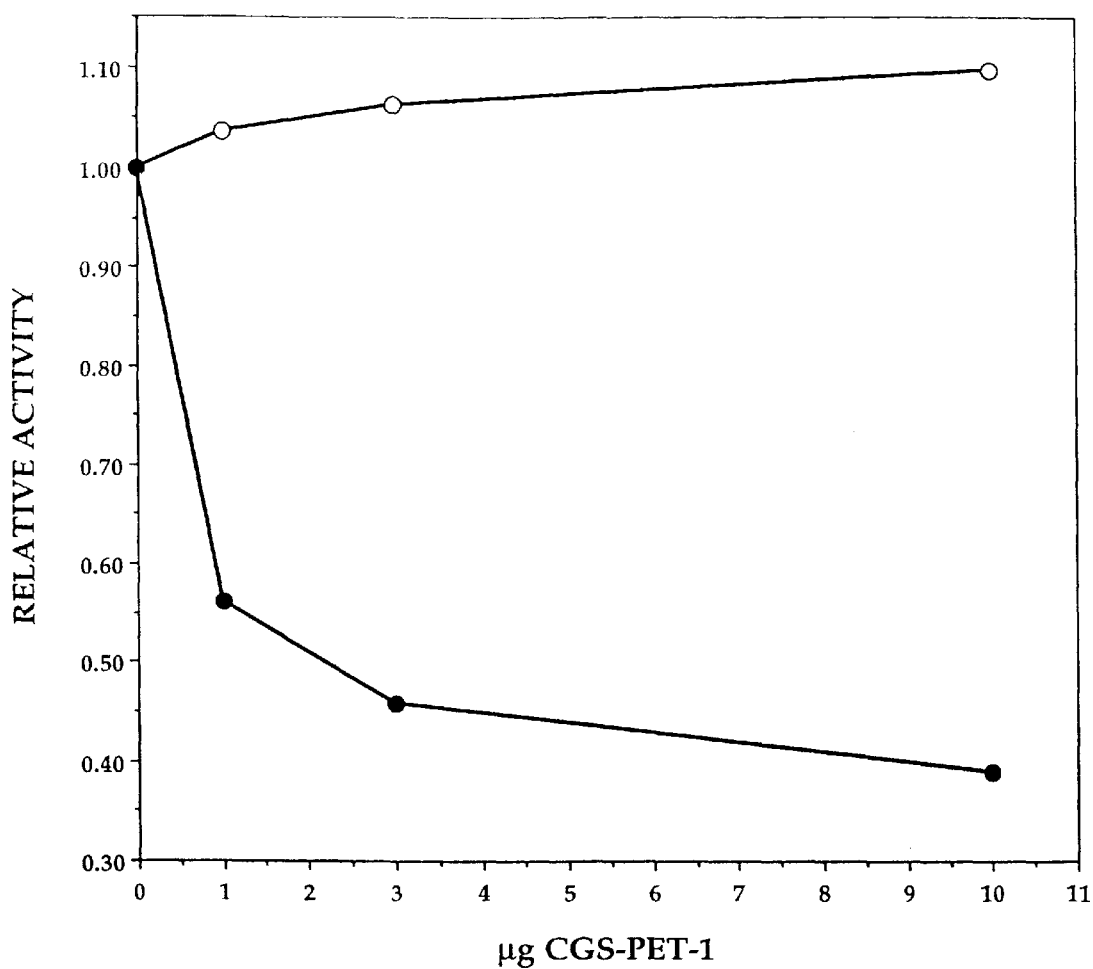

FIG. 6 shows that Pet-1 can repress reporter transcription in an ETS binding site-dependent manner. Luciferase reporters (10 $\mu$g) were cotransfected with the indicated amounts CGS-Pet-1 effector in C6 cells. In reporter 3XP$\alpha$3(−238/+47)-luc (filled circles) transcription of luciferase gene is driven by minimal $\alpha$3 promoter with three tandomly repeated consensus PEA3 binding sites upstream. Reporter 3XPm$\alpha$3(−238/+47)-luc (unfilled circles) is identical to 3XP$\alpha$3(−238/+47)-luc, except GGA core motifs in all three ets binding sites are mutated to tcA (see Experimental Procedures). Relative activities were corrected for transfection efficiency by measuring $\beta$-galactosidase activity expressed from a co-transfected RSV-$\beta$gal plasmid and normalized to basal activities of both reporters without CGS-Pet-1 effector.

Figure 7:
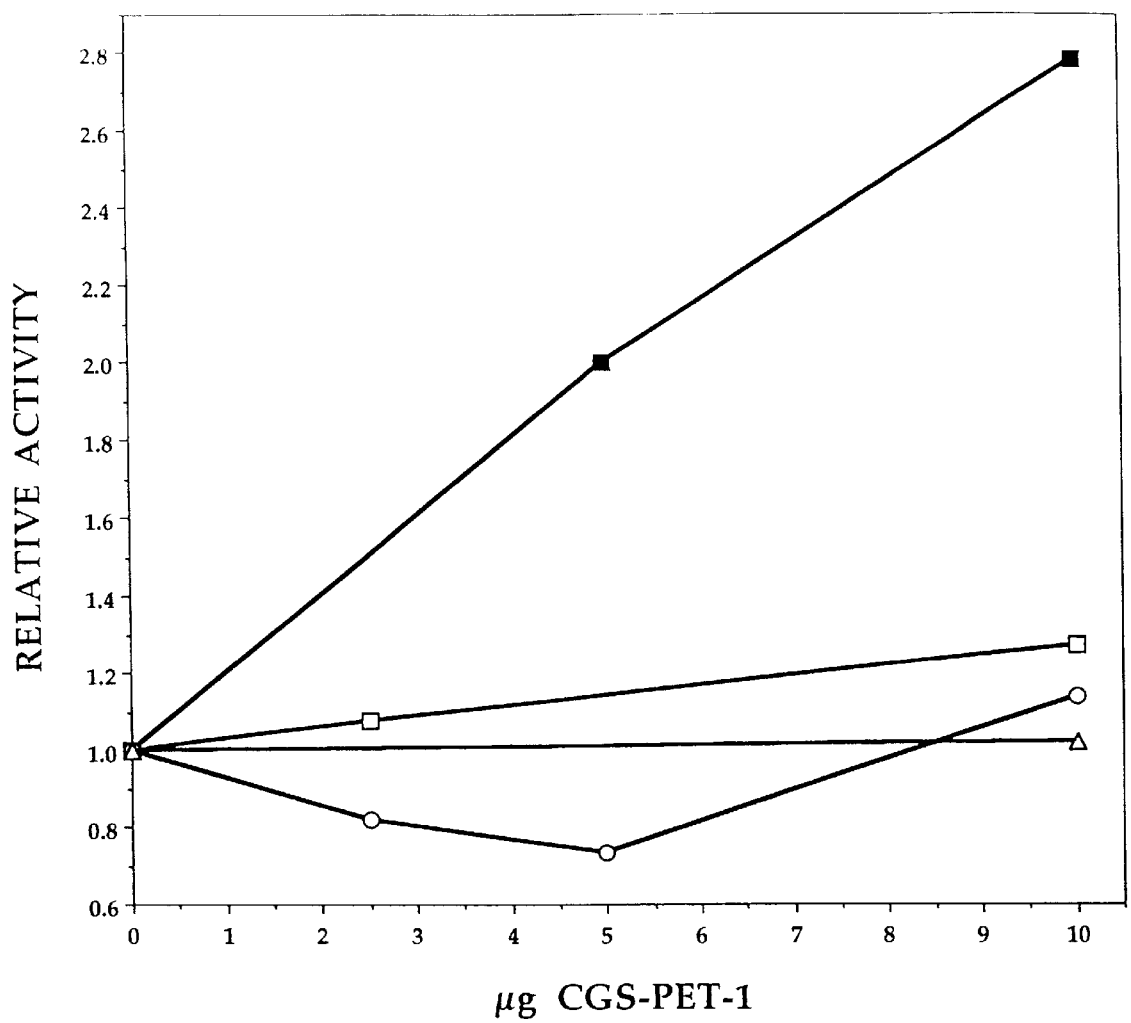

FIG. 7 shows that Pet-1 activates the $\beta$43' enhancer in a cell-type specific manner. Cell-type specific activation of the $\beta$43' enhancer by Pet-1. C6 (filled squares), Rat-2 (unfilled squares), 3T3 (circles), and HeLa (triangles) cells were transfected in parallel with the $\alpha$3 minimal promoter reporter bearing three copies of the $\beta$43' enhancer. The same reporter and effector plasmid preparations were used for all transfections. The dose responses are presented as the luciferase activity of the enhancer-containing reporter divided by that of the $\alpha$3 minimal promoter (no enhancer) for each of the indicated quantities of CGS-Pet-1. The value of this ratio in the absence of CGS-Pet-1 was set to 1. No activation of the $\alpha$3 minimal promoter was observed in any of the co-transfections. The data were corrected for differences in transfection efficiency by measuring the activity of a co-transfected RSV-$\beta$gal reporter. Results similar to those presented were obtained in two additional independent experiments.

Figure 8:
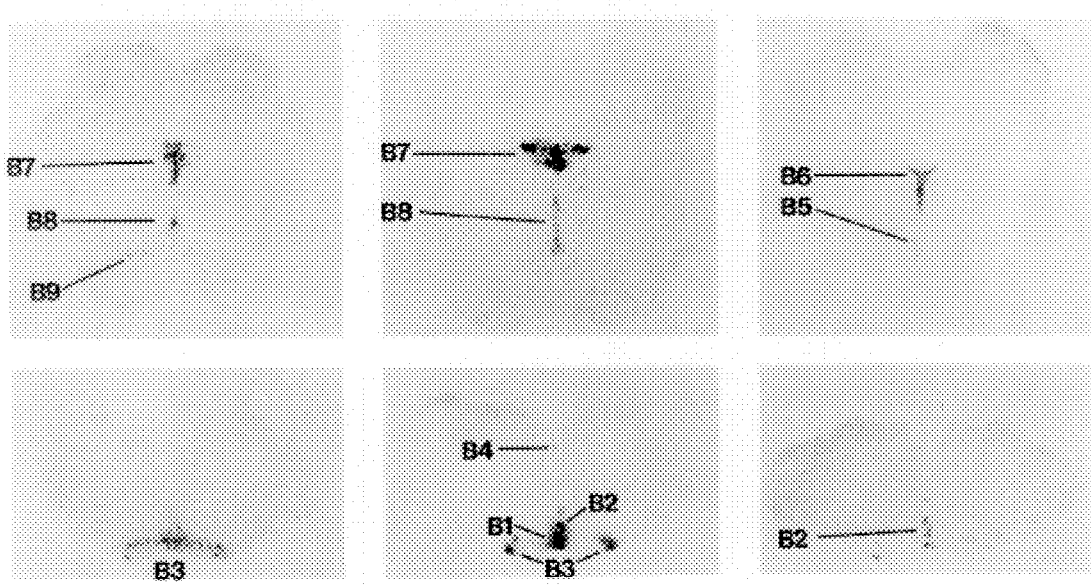

FIG. 8 shows that Pet-1 RNA is expressed in the B1–B9 groups of central serotonergic neurons clusters. The data are presented as X-ray film autoradiography of [35S]-labeled probe in coronal sections of adult rat brain. The Pet-1 RNA distribution corresponds to the B1–B9 groups of 5-HT neuronal clusters (Halliday, G., Harding, A., and Paxinos, G. (1995) in *The rat nervous system* (Paxinos, G. ed), 2nd Ed., pp. 929–974, Academic Press, San Diego; Jacobs, B. L., and Azmitia, E. C. (1992) *Physiological Reviews* 72:165–220). Analyses of several rat brains from olfactory bulbs to spinal cord did not reveal other significant sites of Pet-1 RNA expression in the adult rat brain. B1, raphe pallidus and caudal ventrolateral medulla; B2, raphe obscurus; B3, raphe magnus, rostral ventrolateral medulla, lateral paragigantocellular reticular nucleus; B4, central gray of the medulla oblongata; B5, pontine median raphe nucleus; B6, pontine dorsal raphe nucleus; B7, midbrain dorsal raphe nucleus; B8, midbrain median raphe nucleus; B9, medial lemniscus.

Figure 9:
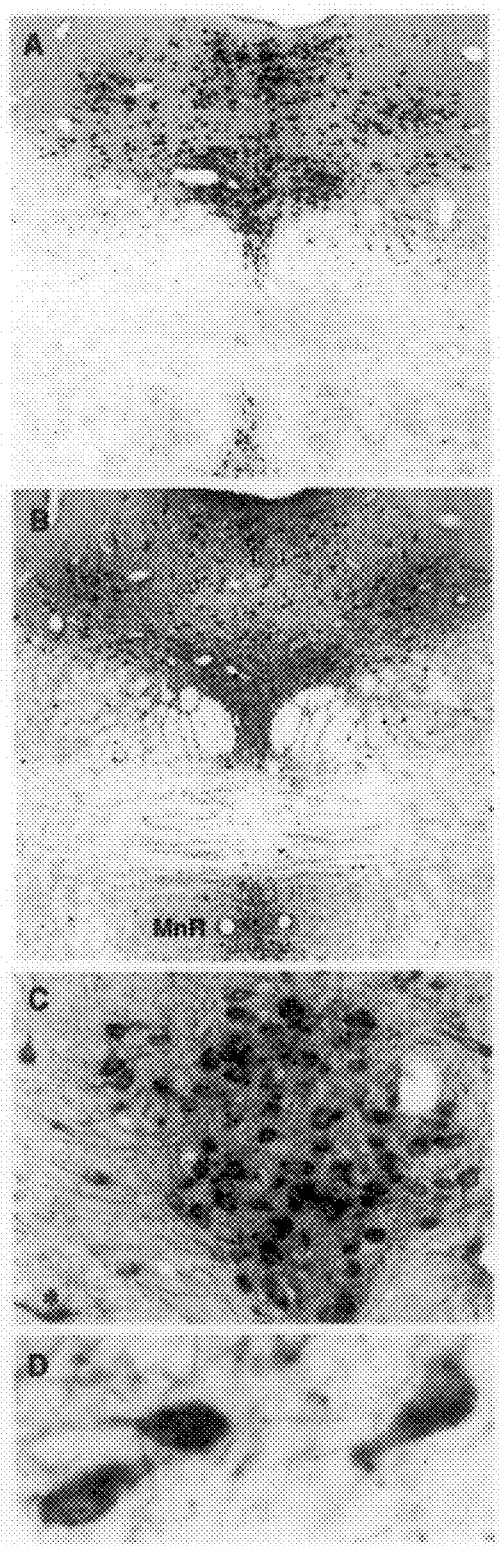

FIG. 9 shows that Pet-1 expression in brain is restricted to serotonergic neurons. A, B) DIG-Pet-1 antisense RNA probe (A) were used to the compare the distribution of Pet-1 RNA to that of 5-HT immunoreactivity (B) in adjacent 20 $\mu$m coronal sections through adult dorsal and median raphe. C,D) Double-label analysis at the level of the ventral field of the dorsal raphe using DIG-Pet-1 RNA probe and a monoclonal raised against rabbit tryptophan hydroxylase. Dark blue reaction product represents Pet-1 RNA and brown reaction product represents TPH immunoreactivity. MnR, median raphe. Asterisk, isolated double labeled neuron in the reticular formation.

Figure 10:
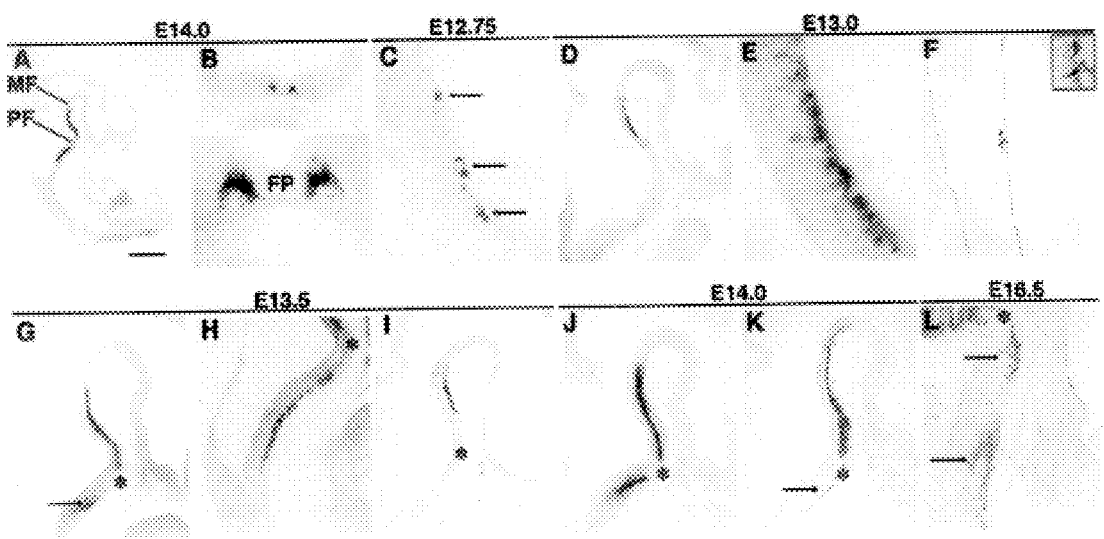

FIG. 10 shows that Pet-1 gene expression in the developing hindbrain precedes the appearance of 5-HT positive neurons. A) In situ hybridization for Pet-1 with digoxigenin-labeled riboprobe at E14.0. Hybridization of a sagittal section close to the midline indicates two domains of Pet-1 expression with one just caudal to the mesencephalic flexure (rostral domain) and the other caudal to the pontine flexure (caudal domain). B) Hybridization of a transverse section of the neural tube at E14.0 shows that Pet-1 expression is limited to two bilateral clusters (top) which are located adjacent to the floorplate and near the outer surface of the ventricular zone (bottom). C) Pet-1 expression at E12.75 in scattered cells (arrows) caudal to the mesencephalic flexure. D) At E13.0 on sagittal, Pet-1 expression is seen as a single longitudinal band caudal to the mesencephalic flexure. E) At higher magnification the Pet-1 positive cells shown in D can be seen near the outer surface of the ventricular zone. F) 5-HT immunohistochemistry reveals the first appearance of 5-HT positive neurons at E13.0 caudal to the mesencephalic flexure; inset shows the morphology of the two cells from this field (dashed lines indicate boundaries of the neural tube). G, H) At E13.5 a caudal domain of Pet-1 expression appears caudal to the pontine flexure (arrow). I) At E13.5, 5-HT positive neurons form a longitudinal band caudal to the mesencephalic flexure, which comprises the rostral 5-HT cluster (box) but the caudal 5-HT cluster is not yet evident. J, Pet-1 expression at E14.0. K) At E14.0 5-HT positive neurons form an extensive rostral cluster and the first 5-HT positive neurons of the caudal group appear below the pontine flexure (arrow). L) More 5-HT neurons appear in the caudal cluster at E16.5. Abbreviations: MF, mesencephalic flexure; PF, pontine flexure; FP, floorplate. Asterisks, pontine flexure.

Figure 11:
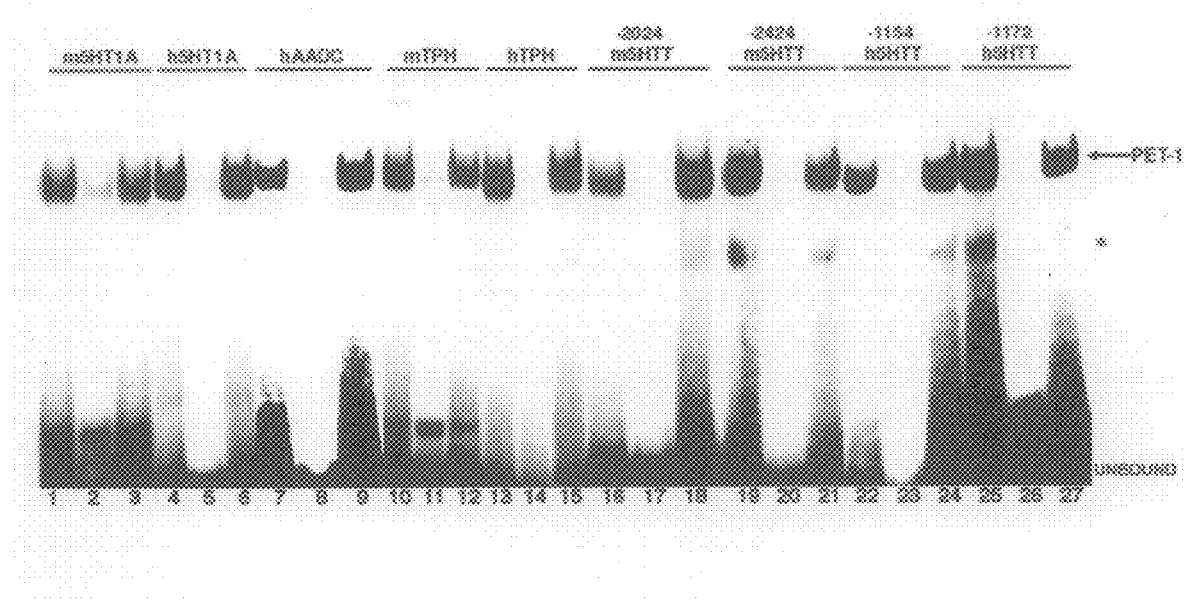

FIG. 11 shows identification of Pet-1 binding sites in serotonergic genes. Mobility shift assays were performed with bacterially expressed Pet-1 protein and oligonucleotides composed of sequences obtained from each of the indicated genes. The potential Pet-1 binding site present in each of these probes is shown in Table 1.

Candidate Pet-1 binding sites were identified based on similarity to the polyomavirus enhancer activator site 3 (PEA3). The consensus binding site is based on sequences listed below, which show strong Pet-1 binding by mobility shift assay. Comparisons indicate that in addition to the invariant GGA core other obligatory nucleosides are thymidine at position +6 and adenosine or guanosine at position +4. Position +1 is the first guanosine residue in the invariant core. 5HT1aR, serotonin receptor 1a; TPH, tryptophan hydroxylase; 5HTT, serotonin transporter; AADC, aromatic L-amino-acid decarboxylase; h, human; m, mouse. Numbers in parentheses indicate positon of a Pet-1 binding site in the 5' flanking region of the indicated gene.

TABLE 1

Pet-1 binding sites in serotonergic genes

| Site | Sequence | |
|---|---|---|
| PEA3 | AGCAGGAAGTG | (SEQ ID NO:3) |
| h5HT1aR (−137/−127) | AGCAGGAAGTT | (SEQ ID NO:4) |
| m5HT1aR (−142/−132) | AGCGGGAAGTT | (SEQ ID NO:5) |
| h5HTT (−1172/−1162) | GAAAGGAAATA | (SEQ ID NO:6) |
| h5HTT (−1154/−1144) | GATAGGAAGTA | (SEQ ID NO:7) |
| m5HTT (−2424/−2414) | CCCAGGAAATG | (SEQ ID NO:8) |
| m5HTT (−2024/−2014) | GGGAGGAAATG | (SEQ ID NO:9) |
| hTPH (−1154/−1144) | ATACGGAAATT | (SEQ ID NO:10) |
| mTPH (−790/−780) | TACAGGATATA | (SEQ ID NO:11) |
| AADC (Intron 1) | TTCAGGAAATT | (SEQ ID NO:12) |
| CONSENSUS Pet-1 | RRMAGGAARTR tttc        t ccgg | |

Analysis of each binding site included incubation with indicated probe and Pet-1 protein (lanes 1, 4, 7, 10, 13, 16, 19, 22, 25), competition of probe and Pet-1 protein interaction with 200–400 molar excess of unlabeled PEA3 oligonucleotides (lanes 2, 5, 8, 11, 14, 17, 20, 23, 26), and competitions of probe and Pet-1 protein interaction with unlabeled oligonucleotides in which the 5'-GGA core of the PEA3 binding site was changed to 5'-TAC (lanes, 3, 6, 9, 12, 15, 18, 21, 24, 27). Details of binding reactions and competitions are described in Material and Methods. Asterisk, complex formed with probe and a Pet-1 protein degradation product.

FIG. 12 shows functional analysis of the Pet-1 binding sites. A) Four copies of the mouse −2024/−2014 5-HTT Pet-1 binding site and two copies of the human −1172/−1162; −1154/−1144 tandem Pet-1 binding site were each cloned upstream of the adenovirus major late promoter (MLP) to prepare 4xm5HTT-luc and 2xh5HTT-luc, respectively. These reporters were transfected into dissociated retinal cultures along with CMV-Pet-1-VP16 effector by calcium phosphate precipitation as described in Material and Methods. Filled bars represent the ratio of indicated reporter activities over MLP basal activity obtained in co-transfections with empty CMV plasmid. Cross-hatched bars represent the ratio of indicated reporter activities over MLP basal activity obtained in co-transfections with CMV-Pet-1VP16 effector normalized to the ratio obtained in empty CMV plasmid co-transfections. Error bars are ±sem. B) PC12 cells were transfected with reporters carrying either MLP, four copies of the 5-HT1a receptor Pet-1 binding site placed immediately upstream of MLP (4x5HT1a-luc) or four copies of the 5-HT1a receptor site upstream of MLP except that each copy had TAC residues in place of the GGA core (mut4x5HT1a-luc). PC12 cell transfections were performed by electroporation as described (Yang, X., et al., *J. Biol. Chem.* 269:10252–10264, 1994). Data are the average of four separate transfections for each reporter and represent the mean relative light units ±SD.

DETAILED DESCRIPTION OF THE INVENTION

ETS domain proteins are a class of sequence-specific transcription factors that are also important for regulating vertebrate cell phenotypes. The first member of this family to be identified was v-ets-1, which encodes part of an oncogenic gag-myb-est fusion protein in the E26 avian erythroblastosis virus (Le-Prince, D., et al., "A putative second cell-derived oncogene of the avian leukemia retrovirus E26" *Nature* 306:395–397, 1983; Nunn, M. K., et al., "Tripartite structure of the avian erythroblastosis virus E26 transforming gene" *Nature* 306:391–395, 1983). The defining characteristic of the vEts oncoprotein and the greater than 30 other ETS transcription factors subsequently identifies is a highly conserved ~85 amino acid, winged helix-turn-helix DNA binding domain termed the ETS domain (Donaldson, L. W., et al., "Solution structure of the ETS domain from murine Ets-1: a winged helix-turn-helix DNA binding motif" *EMBO J.* 15:125–134, 1996). Several ETS factors have been implicated in the cell type-specific transcription of genes expressed within the hematopoietic lineage (Wasylyk, B., et al., "The Ets family of transcription factors" *Eur. J. Biochem.* 211:7–18, 1993). Some ETS-domain factors are also expressed in vertebrate and invertebrate nervous systems, which points to a role for ETS factors in the development and maintenance of neural cell phenotypes. Indeed, two Drosophila ets genes, Pointed and Yan, act antagonistically in R7 photoreceptor neuron induction and differentiation (O'Neill, E. M., et al., "The activities of two Ets-related transcription factors required for Drosophila eye development are modulated by the Ras/MAPK pathway" *Cell* 78:137–147, 1994; Treier, M., et al., "JUN cooperates with the ETS domain protein Pointed to induce photoreceptor R7 fate in the Drosophila eye" *Cell* 83:753–760, 1995). However, in contrast to other classes of transcription factors, relatively little attention has been given to the expression and function of various ETS domain factors in the vertebrate nervous system.

A cluster of neuronal nicotinic acetylcholine receptor (nAchR) subunit genes, ordered β4, α3 and α5, are expressed in highly restricted patterns in the vertebrate peripheral and central nervous systems (Boulter, J., et al., "α3, α5 and β4: three members of the rat neuronal nicotinic acetylcholine receptor-related gene family form a cluster" *J. Biol. Chem.* 265:4472–4482, 1990; Couturier, S., et al. "a5, a3, and non-a3: Three clustered avian genes encoding neuronal nicotinic acetylcholinereceptor-related subunits" *J. Biol. Chem.* 265:17560–17567, 1990). These genes encode subunits that are assembled into excitatory neurotransmitter receptors in sympathetic and parasympathetic postganglionic neurons as well as in the adrenal medulla (McGehee, D. S., and Role, L. W., "Physiological diversity of nicotinic acetylcholine receptors expressed by vertebrate neurons" *Annu. Rev. Physiol.* 57:521–546, 1995; Sargent, P. B., "The diversity of neuronal nicotinic acetylcholine receptors" *Annu. Rev. Neurosci.* 16:403–443, 1993). With regard to the transcriptional mechanisms that regulate these clustered genes, we have recently identified a novel enhancer in the 3'-untranslated exon of the neuronal nAchR 62 4 subunit gene (McDonough, J., and Deneris, E., "b43': an enhancer displaying neural-restricted activity is located in the 3'-untranslated exon of the rat nicotinic acetylcholine receptor b4 gene" *J. Neurosci.* 17:2273–2283, 1997). The β43' enhancer is active in a cell type-specific manner and, therefore, it is likely to participate in the regulation of restricted expression patterns of one or more of the clustered neuronal nAchR subunits genes. Present within the β43' enhancer are consensus ETS-domain factor DNA-binding sites, which raises the possibility that members of this transcription factor family participate in regulating neuronal nAchR subunit gene expression. Among the cell lines tested, the β43' enhancer has significant activity only in the PC12 neuroendocrine line. This tumor line is derived from rat adrenal chromaffin cells and strongly expresses each of the clustered neuronal nAchR genes (Boulter, J., et al., "α3, α5 and β4: three members of the rat neuronal nicotinic acetylcholine receptor-related gene family form a cluster" *J. Biol.*

Chem. 265:4472–4482, 1990). Therefore, we analyzed ets transcripts in PC12 cells to identify possible trans-acting regulators of clustered nAchR genes.

Our screen for ets transcripts in PC12 cells was initiated as means to find potential cell-type specific trans-acting regulators of the clustered neuronal nAchR genes. We focused first on ets genes because two consensus ETS-domain binding sites were identified in the β43' enhancer. Activity of the enhancer is cell-type specific and is strongest in the PC12 line. These findings indicate that β43' activity is correlated with the expression pattern of the clustered neuronal nAchR genes in cell lines and therefore is likely to interact with cell-type specific transcription factors (McDonough, J., and Deneris, E., "b43': an enhancer displaying neural-restricted activity is located in the 3'-untranslated exon of the rat nicotinic acetylcholine receptor b4 gene" *J. Neurosci.* 17:2273–2283, 1997). The restricted expression pattern of Pet-1 establishes it as a possible regulator of cell-type specific gene expression. Similar to expression of clustered neuronal nAchR genes, Pet-1 expression in cell lines correlated with β43' enhancer activity. In addition to co-expression of the clustered nAchR genes and Pet-1 in PC12 cells and adrenal medulla, we obtained functional evidence supporting the hypothesis that Pet-1 is a positive transcriptional regulator of neuronal nAchR genes. Pet-1 can activate transcription in a β43' enhancer dependent manner. Although Pet-1 was able to activate transcription in a β43'-dependent manner we were unable to detect binding of in vitro translated Pet-1 protein to the enhancer repeats. One possibility is that Pet-1 must be post-translationally modified before it can bind sequences in the enhancer. A second possibility, discussed below, is that Pet-1 must be recruited to the DNA through protein-protein interactions with other sequence-specific transcription factors.

Our findings show that Pet-1 can either repress or activate transcription in the same cell type. Thus, the activity of Pet-1 is likely to depend on the composition of particular DNA binding elements within the regulation region of target genes. Repression was observed in all lines tested (C6, Rat2, HeLa, NIH3T3) whereas activation was seen only in C6 cells. These results indicate that the activity of Pet-1 as a transactivator may also depend on protein-protein interactions with other sequence-specific partners. The β43' enhancer is nearly 90 bp in length and preliminary data indicate that in addition to the consensus ETS binding sites other sequences in the enhancer are also important for its activity. Therefore, the enhancer may be a composite DNA binding interface such that transactivation by Pet-1 requires interaction with co-factors that are also expressed in a cell-type specific manner. The idea that Pet-1 function depends on protein-protein interactions with factors that bind to other sites in the β43' enhancer seems plausible in view of the dependence for DNA binding of various ETS domain factors on interactions with distinct co-factors. For example, full activity of the growth factor-inducible serum response element (SRE) in the c-fos proto-oncogene requires binding of the serum response factor (SRF) as well as a distinct factor called the ternary complex factor. The ETS factors, SAP1 and Elk-1 both exhibit ternary complex factor activity but show little or no binding to the SRE unless recruited to the DNA by SRF (Dalton, S., and Treisman, R., "Characterization of SAP-1, a protein recruited by serum response factor to the c-fos serum response element" *Cell* 68:597–612, 1992; Hill, C. S., et al., "Functional analysis of a growth factor-responsive transcription factor complex" *Cell* 73:395–406, 1993; Hipskind, R. A., et al., "Ets-related protein Elk-1 is homologous to the c-fos regulatory factor p62TCF" *Nature* 354:531–534, 1991; Shaw, P. E., et al., "The ability of a ternary complex to form over the serum response element correlates with serum inducibility of the human c-fos promoter" *Cell* 56:563–572, 1989). Similarly, the binding of the ETS factors, Net or Elk-1, to an ETS/Paired box composite DNA binding site in the early B-cell-specific mb-1 promoter requires recruitment by the paired box factor, Pax-5 (Fitzsimmons, D., et al., "Pax-5 (BSAP) recruits Ets proto-oncogene family proteins to form functional ternary complexes on a B-cell-specific promoter" *Genes Dev.* 10:2198–211, 1996). In the context of the present invention, Pet-1 has been shown to be functional in several cell types thereby enabling its use in a variety of assay systems.

In the present invention it is shown that expression of the ETS domain factor, Pet-1, in the brain is limited to the serotonergic system. Serotonin plays a crucial neuromodulatory role in numerous physiological and behavioral functions, and dysfunction of the serotonergic system has been implicated in several psychiatric disorders. In the adult, Pet-1 marks the entire rostro-caudal extent of the midbrain/hindbrain raphe system and localizes virtually exclusively to 5-HT neurons. Its onset of expression precedes the appearance of the 5-HT in the developing neural tube by about a half day. At least one conserved Pet-1 binding site is present in or near the promoter regions of several genes whose expression is characteristic of the serotonergic phenotype. Pet-1 binding sites are capable of supporting transcriptional activation through interactions with the Pet-1 ETS domain and multimerization produces a strong enhancer. Together our findings establish Pet-1 as an early and precise marker of 5-HT neurons and suggest that it functions in the terminal differentiation and maintenance of central serotonergic neuron phenotype.

In a survey of various tissues, Pet-1 RNA expression could be detected only in adrenal medulla, eye, intestine, and brain. To begin to understand the functions Pet-1 might perform in the nervous system, we have investigated Pet-1 expression in the adult and developing brain. We find that, at all developmental ages, Pet-1 expression in the brain is limited to the 5-HT neurotransmitter system. We also identified a conserved transcriptional cis-element present in or near genes whose expression is characteristic of mature central serotonin neurons. Together our results identify Pet-1 as a crucial transcriptional regulator of genes required specifically for serotonergic phenotype.

The deduced primary structure of Pet-1 includes a highly conserved ETS DNA binding domain that is most closely related to the ERG subfamily (Wasylyk, B., "The Ets family of transcription factors" *Eur. J. Biochem.* 211:7–18, 1993) of ETS-domain factors. Subsequent to our characterization of the Pet-1 primary structure Peter et al. reported a new human ETS family member called FEV (Peter, M., et al., "A new member of the ETS family fused to EWS in Ewing tumors" *Oncogene* 14:1159–1164, 1997). Pet-1 and FEV share an identical ets DNA binding domain. However, these ETS-related factors are not identical outside the DNA binding domain. First, there are seven amino-acid differences in their carboxy-terminal regions. Second, Pet-1 extends 103 amino-acids longer than FEV on the amino-terminal end. The expression pattern of Pet-1 and FEV also appears somewhat different. Thus it is not clear whether Pet-1 and FEV are distinct genes or species variants of the same gene.

Most ETS family members are expressed widely in embryonic and adult tissues, which suggests that these factors help to control gene expression in a wide variety of cell lineages. Some members such as Ets-1 (Sacchi, N., et al., "Single-cell detection of ets-1 transcripts in human neuroectodermal cells" *Oncogene* 6:2149–2154, 1991), PEA3 (Xin, J.-H., et al., "Molecular cloning and characterization of PEA3, a new member of the Ets oncogene family that is differentially expressed in mouse embryonic cells" *Genes Dev.* 6:481–496, 1992), ER81 (Brown, T. A., and McKnight, S. L., "Specificities of protein-protein and protein-DNA interaction of GABPα and two newly defined ets-related proteins" *Genes Dev.* 6:2502–2512, 1992; Monte, D., et al., "Molecular characterization of the ets-related human transcription factor ER81" *Oncogene* 11:771–779, 1995) and ERM (Monte, D., et al., "Molecular cloning and characterization of human ERM, a new member of the Ets family closely realted to mouse PEA3 and ER81 transcription factors" *Oncogene* 9:1397–1406, 1994) are expressed strongly in the nervous system. Analysis of Pet-1 expression suggests that Pet-1 is involved in the regulation of gene transcription in specific neural cell populations. The Pet-1 gene is expressed at very high levels in neuroendocrine-derived PC12 cells. Based on RNase protections and clone frequency in library screens, we estimate that Pet-1 mRNA constitutes about 0.01% of all PC12 polyadenylated RNA. In contrast, a survey of several other cell lines showed no Pet-1 expression. Of the tissues examined, Pet-1 expression was highest in the adrenal gland. Somewhat lower levels of expression were detected in brain, intestine, and eye. Pet-1 RNA was not detected in other tissues examined, which indicates that the expression pattern of this ets gene is highly restricted. In contrast, FEV was not detected in brain but showed expression in heart (Peter, M., et al. "A new member of the ETS family fused to EWS in Ewing tumors" *Oncogene* 14:1159–1164, 1997). Expression of Pet-1 in the adrenal medulla is consistent with expression in PC12 cells as this line is derived from adrenal chromaffin cells. Interestingly, Pet-1 gene expression was not detected in superior cervical ganglia (SCG). Because neural cells within the adrenal gland and SCG arise from the sympathoadrenal sublineage of post-migratory neural crest (Anderson, D. J. "The neural crest cell lineage problem: neuropoiesis?" *Neuron* 3:1–12, 1989), the differential expression of Pet-1 in these tissues raises the possibility that Pet-1 is a regulator of terminal differentiation, perhaps by stabilizing the chromaffin cell phenotype.

Additional research has shown that the ETS-domain factor Pet-1 is a rare example of a vertebrate transcription factor gene showing an extremely restricted neuronal expression pattern in the brain. This pattern is striking as it appears to be limited to the cell bodies of the midbrain/hindbrain serotonergic neurotransmitter system. No other Pet-1 positive cells could be identified in the brain although we cannot rule out the possibility that small numbers of widely scattered Pet-1 positive cells may have gone undetected in other regions of the brain. Nevertheless, these findings together with the detection of Pet-1 expression beginning just prior to terminal differentiation of 5-HT neurons and the presence of transcriptionally active Pet-1 binding sites in or near the promoter regions of several genes whose coordinate 5-HT neuron-specific expression characterize the mature serotonergic neuron phenotype suggest that Pet-1 is an essential component of a transcriptional program directing central 5-HT neuron differentiation. As Pet-1 RNA is detected in the intestine (Fyodorov, D., et al., *J. Neurobiol.* 32:151–163, 1998) it is possible that Pet-1 is also expressed in the only other major population of vertebrate 5-HT neural cells, enterochromaffin cells and serotonergic enteric interneurons (Gershon, M. D. (1991) in *Kynurenine and Serotonin Pathways*. (Schwarcz, R., ed) eds), pp. 221–230., Plenum Press, New York.).

The generation of 5-HT neurons in the neural tube depends, in part, on the activity of the notochord and floor plate-derived secreted signaling molecule Sonic hedgehog (Shh) (Ye, W., et al., *Cell* 93:755–766, 1998). Two downstream targets of the Shh signaling pathway, Nkx2.2 and Gli2, have been implicated in the development of subsets of hindbrain 5-HT neurons. Elimination of the homeobox gene, Nkx2.2, results in the absence of a subset of serotonergic neurons in rhrombomere 2 of the hindbrain (Briscoe, J., et al., *Nature* 398:622–627, 1999) while elimination of the zinc-finger transcription factor Gli2 results in a partial loss and abnormal location of remaining 5-HT neurons in the ventral midline (Matise, M. P., et al., *Development* 125:2759–2770, 1998). A third transcription factor GATA-3 is thought to play a role in the development of some caudal raphe nuclei. GATA-3 is expressed broadly during embryogenesis including many but not all raphe 5-HT neurons (Hikke van Doorninck, J., et al., *J. Neurosci.* 19:1–8, 1999). In chimeric GATA-3 homozygous null mice the organization of cells in the raphe obscurus appears altered compared to wild type mice (Hikke van Doorninck, J., et al., *J. Neurosci.* 19:1–8, 1999). In addition to 5-HT neurons, each of these three factors have been implicated in the development of several other types of neuronal or non-neuronal cells. Furthermore, Nkx2.2 and Gli2 function during very early stages of neurogenesis in spinal cord, hindbrain, and midbrain (Briscoe, J., et al., *Nature* 398:622–627, 1999; Matise, M. P., et al., *Development* 125:2759–2770, 1998). In contrast, Pet-1 is the first transcription factor gene showing an expression pattern in the brain that is limited to 5-HT neurotransmitter system. This suggests that Pet-1 unlike these other transcription factors may perform a strictly serotonergic-specific function.

While the present invention is not limited to any particular mechanism, our findings, raise the intriguing possibility that Pet-1 functions in a manner analogous to the Phox2a and Phox2b transcription factors (Goridis, C., and Brunet, J.-F., *Curr. Opin. Neurobiol.* 9:47–53, 1999). These closely related paired-like homeodomain proteins are expressed in all central and peripheral noradrenergic neurons just as these neurons are acquiring their differentiated phenotype (Tiveron, M.-C., et al., *J. Neurosci.* 16:7649–7660, 1996; Pattyn, A., et al., *Development* 124:4065–4075, 1997). Phox2a/Phox2b binding sites contribute to dopamine-b-hydroxylase (DBH) promoter activity and forced expression of each of these factors can activate the promoter in DBH-negative cell lines (Swanson, D. J., et al., *J. Biol. Chem.* 272:27382–27392, 1997; Yang, C., et al., *J. Neurochem.* 71:1813–1826, 1998; Kim, H.-S., et al., *J. Neurosci.* 18:8247–8260, 1998). Moreover, loss of function experiments demonstrate that both of these factors are essential determinants of noradrenergic phenotype (Morin, X., et al., *Neuron* 18:411–423, 1997; Pattyn, A., et al., *Nature* 399:366–370, 1999).

Expression of the bicoid-related homeodomain protein, Ptx3, in the developing and adult brain is also limited to a single neurotransmitter neuronal cell type; in this case mesencephalic dopaminergic neurons (Smidt, M. P., et al., *Proc. Natl. Acad. Sci, USA* 94:13305–13310, 1997). The onset of Ptx3 expression in the ventral surface of the mesencephalic flexure at E11.5 in the mouse coincides with the appearance of the first tyrosine hydroxylase-positive cells in this region of the neural tube. Ptx3 has, therefore, been proposed to be a crucial regulator of dopaminergic phenotype. However, in vivo loss of function experiments have not yet been reported for this gene. Similarly, loss or gain of function experiments should help to reveal what role Pet-1 performs in the development of the serotonergic neurotransmitter system and may create novel animal models for clinical disorders involving this system. Thus, the identification of Pet-1 expression in the brainstem 5-HT system is quite likely to be an important step in elucidating the molecular mechanisms governing the development of this vital neurotransmitter system.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., elcetroporation, lipofection). Generally enzymatic reactions and purification steps are performed according to the manufacturer's specifications. The techniques and procedures are generally performed according to conventional methods in the art and various general references [See, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., New York].

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCI buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

The present invention contemplates assays for detecting the ability of agents to inhibit or enhance Pet-1 modulation of central serotonin 5-HT neurons where high-throughput screening formats are employed together with large agent banks (e.g., compound libraries, peptide libraries, and the like) to identify antagonists or agonists. Such Pet-1 antagonists and agonists may be further developed as potential therapeutics and diagnostic or prognostic tools for diverse types of cancers, autoimmune diseases and hereditary diseases.

1. Screens to Identify Agonists of Antagonists of Pet-1

There are several different approaches contemplated by the present invention to look for small molecules that specifically inhibit or enhance the ability of Pet-1 to modulate apoptosis. One approach is to transfect expression constructs comprising nucleic acid encoding Pet-1 into cells and measure changes in the rate of serotonergic activity as compared to controls after the cells have been exposed to the compound suspected of modulating mediating Pet-1 activity. Cells may be transiently transfected or stably transfected with the construct under control of an inducible promoter. Other embodiments would include translation of the invention and purification of the peptide. The purified peptide could then be used to test specific compound:protein interactions. Additionally, it is possible to generate antibodies to the translated invention allowing for the development of immunological assays such as, but not limited to, RIA, ELISA or Western blot. Furthermore, transgenic animal could be produced allowing for in vivo assays to be conducted.

A. In vitro Assays a. Transfection Assays

Transfection assays allow for a great deal of flexibility in assay development. The wide range of commercially available transfection vectors will permit the expression of the Pet-1 gene of the present invention in a extensive number of cell types. In one embodiment, cells are transiently transfected with an expression construct comprising nucleic acid encoding Pet-1 of the present invention that included an inducible promotor allowing for the initiation of translation and transcription when needed. Cells are exposed to the agent suspected of modulating Pet-1 activity, Pet-1 expression is turned on and serotonergic activity is measured. Rates of serotonergic activity in cells expressing the invention are compared to rates of serotonerg activity in cells transfected with cells expressing a control expression vector (e.g. an empty expression vector). Rates of serotonergic activity can be quantitated by any of a number of ways reported in the literature and known to those practiced in the art.

In another embodiment, stably transfected cells lines are developed, i.e. cell lines stably expressing the Pet-1 cDNA of the present invention. The use of an inducible promoter would be utilized in these systems. Screening assays for compounds suspected of modulating Pet-1 activity are conducted in the same manner as with the transient transfection assays. Using stably transfected cell lines allows for greater consistency between experiments and allows for inter-experimental comparisons.

B. In Vivo Assays a. Transgenic Animal Assays

In one embodiment, transgenic animals will be constructed using standard protocols. The generation of transgenic animals will allow for the investigation of diseases for which the over expression of Pet-1 may provide the means for determining the physiology of the disease or its treatment.

2. Screen to Identify Cells Expressing Similar or Homologous Genes

In one embodiment screens will be constructed using solid supports such as microassay microchip techniques. This will allow for the development of a high-through-put screen for the identification of cells expressing genes similar to, or homologous with, the Pet-1 gene.

3. Screens to Identify Pet-1 Interactive Molecules

A. In vitro Assays

There are several different approaches to identifying Pet-1 interactive molecules. Such proteins may regulate Pet-1 function. Techniques that may be used are, but not limited to, immunoprecipitation of Pet-1 with antibodies generated to the transcription product of the invention. This would also bring down any associated bound proteins. Another method is to generate fusion proteins containing Pet-1 connected to a generally recognized pull-down protein such as glutathione S-transferase. Bound proteins can then be eluded and analyzed.

a. Immunoprecipitation

After the generation of antibodies to Pet-1, cells expressing transfected Pet-1 are lysed and then incubated with one of the antibodies. Antibodies with the bound Pet-1 and any associated proteins can then be pulled down with protein-A Sepharose or protein-G Sepharose beads, using standard techniques.

b. Fusion Protein Pull-down

A method similar to immunoprecipitation is to construct fusion proteins of Pet-1 and glutathione S-transferase (GST). The Pet-1 fusion proteins are then incubated with cell extracts and then removed with glutathione Sepharose beads. Any bound, Pet-1 proteins are then characterized.

B. In Vivo Assays a. Yeast Two-hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein.

b. Screens to Identify Pet-1 Homologs

Standard molecular biological techniques can be used to identify Pet-1 homologs in a variety of species. For example, the present invention contemplates a variety of approaches including, but are not limited to, DNA-DNA hybridization techniques (e.g. Southern blots) and DNA-RNA hybridization techniques (e.g. Northern blots). Additional techniques may include, for example, immunoscreening of proteins made from library stocks with antibodies generated to translation products of SEQ ID NO:1. Furthermore, immunoprecipitation of known or suspected interactive proteins of Pet-1 can be followed by the identification of possible mutant Pet-1 homologs with antibodies generated to translation products of SEQ ID NO:1.

EXPERIMENTAL

Materials and Methods

In vitro Amplification of ETS-domain Sequences.

Sequences of 15 mammalian ETS domain proteins were aligned and two highly conserved regions of the ETS-domain [N-terminal, I/V/L)(Q/Y/T)LW(E/Q)FL (SEQ ID NO:13) and C-terminal, MNY(D/E)(K/T)(L/M)(S/G) (SEQ ID NO:14)] were used to prepare degenerate PCR primers with XbaI and KpnI cloning sites. Not every possible codon was used, but instead G and T residues were introduced at degenerate positions to minimize the mismatch effect, and rat codon frequencies were taken into account (Nakamura et al., 1996). Total RNA was isolated from a 150 mm dish of nearly confluent PC12 cells using an RNeasy kit (Qiagen Inc., Chatsworth, Calif.). About 200 µg total RNA was DNase I treated (Boehringer-Mannheim, Indianapolis, Ind.) and poly (A$^+$)-selected with Oligotex (Qiagen Inc.). The poly (A$^+$) RNA was not eluted, but instead cDNA was synthesized in situ on latex particles. We used AMV reverse transcriptase (Boehringer-Mannheim) in standard conditions, except BSA was added to 0.5 mg/ml. The RNA template was eliminated by repeated boiling/washing steps. Latex-coupled oligo-dT cDNA was resuspended in 50 µl TE and used as the PCR template. The Latex-cDNA suspension (5 µl) was primed with 100 ng sense ets primer (5'-GCC TCTA GAK RTK HMK YTK TGG SAG TTT YT) (SEQ ID NO:15) at 45° C. in 100 µl PCR buffer (containing 0.5 mg/ml BSA) and elongated with Taq polymerase (Promega Corp. Madison, Wis.) at the same temperature for 30 min. The cDNA duplex was denatured by boiling. Latex particles were pelleted and the sense strand DNA (10 µl) was used as a template in a 35 cycle "touchdown" PCR reaction (Don et al., 1991) with annealing temperatures in the range of 60 to 50° C. The antisense primer used was 5'-CCCG GTA CCK KSH KAK TKT KTC GTA GTT CAT (SEQ ID NO:16). A single product of expected size (~200 bp) was excised from a 2% agarose gel, purified on glassmilk (QIAEX II, Qiagen Inc.), digested with XbaI and KpnI and purified again. This material was cloned into pGEM-7Zf(+) (Promega Corp.) and ten individual bacterial clones were analyzed by sequencing and conceptual translation in all three reading frames.

Library Screening

A plasmid cDNA library was prepared from PC12 cell RNA using Marathon RACE kit (Clontech, Palo Alto, Calif.). The cDNA was ligated to EcoR1 adapters (Pharmacia Biotech Inc., Piscataway, N.J.), digested with Not1 and ligated into EcoR1/Not1 digested pGEM-11Zf(+) (Promega Corp.). The ligation products was electroporated into supercompetent XL1-Blue cells (Stratagene, La Jolla, Calif.). The 200 bp PCR fragment amplified in the degenerate screen representing a possibly novel ETS domain sequence was random-primed with Multiprime labeling kit (Amersham Corp. Arlington Heights, Ill.) and used to screen about 200,000 colonies that were plated at a density of about 10,000 colonies per 150 mm dish. After transfer to nylon membranes (Qiagen Inc.), denatured DNA in colonies was hybridized to probe in 6X SSC, 7X Denhardt's reagent, 1% SDS overnight and washed at high stringency. One clone (42–11Z) was isolated, which was restriction mapped and partially sequenced.

Because 42-11Z did not appear to encode a full length ETS-domain protein, a 535 bp Blpl/Smal fragment (ets-domain) of p42-11Z was used as a probe to screen a PC12 λgt11 library (Clontech). About 1,000,000 individual plaques were plated on twenty 150 mm dishes and nylon replicas were hybridized as described above. Thirteen clones were analyzed and found to contain inserts ranging from 1.1 to 1.7 kb. The longest insert (in clone λ73) was subcloned into pGEM-7Zf(+) and sequenced on both strands. Two shorter inserts (λ62 and λ81) were also sequenced on both strands to confirm the λ73 sequence. The PHYLIP (Phylogeny Inference Package) software for Macintosh®, version 3.5c (Copyright 1986–1993 by Joseph Felsenstein and by the University of Washington) was used for sequence alignments and parsimony analysis.

In Vitro Translation and EMSA Analysis

Three in vitro translation templates were prepared. Plasmid p73-7Z contains the full-length λ73 cDNA cloned into the EcoR1 site of pGEM-7Zf(+) under the control of the T7 promoter. In plasmid pα73-7Z, 107 bp on the 5' end are deleted by XbaI restriction digest and religation. Plasmid p73-RE contains the full length λ73 cDNA under the translational control of internal ribosomal entry site to enhance cap-independent translation (Jang, S. K., and Wimmer, E., "Cap-independent translation of encephalomyocarditis virus RNA: structural elements of the internal ribosomal entry site and involvement of a cellular 57-kD RNA-binding protein" *Genes Dev.* 4:1560–1572, 1990). Also present in this plasmid are sequences at the 5' end which encode an amino-terminal EE epitope tag, EEEEYMPME (SEQ ID NO:17) (Yan, M., and Templeton, D. J., "Identification of 2 serine residues of MEK-1 that are differentially phosphorylated during activation by raf and MEK kinase" *J. Biol. Chem.* 269:19067–19073, 1994) Pet-1 protein was synthesized in vitro using TNT coupled Rabbit Reticulocyte Lysate system (Promega Corp.).

For EMSA analysis, five pmoles PEA3 (Xin, J.-H., et al., "Molecular cloning and characterization of PEA3, a new member of the Ets oncogene family that is differentially expressed in mouse embryonic cells" *Genes Dev.* 6:481–496, 1992) DNA binding site double stranded oligonucleotide ((GAT CCA GGA AGT GAC (SEQ ID NO:18), top strand and GTC ACT TCC TGG ATC (SEQ ID NO:19), bottom strand; core ETS motifs are underlined)) were radiolabeled with 50 $\mu$Ci [$\gamma$-$^{32}$P]-ATP and T4 polynucleotide kinase (Boehringer) and desalted by G-25 chromatography. In a binding reaction 0.1 pmoles radiolabeled probe (100,000–200,000 cpm), 2 $\mu$l in vitro translated EE-Pet-1, 2 $\mu$g poly(dIdC) and either 0, 2 or 10 pmoles cold competing oligonucleotide in 0.5X Tris-glycine buffer and 10% glycerol were combined simultaneously and incubated at 25° C. for 30 min then loaded on a 6% native polyacrylamide gel (in 0.5X Tris-glycine buffer). Gels were run at 25 mA for 20–30 min, dried and exposed for 1–24 hrs. Wild type PEA3 and mutant PEA3 ((GAT CCA tcA AGT GAC (SEQ ID NO:20), top strand and GTC ACT Tga TGG ATC (SEQ ID NO:21), bottom strand)) double stranded oligonucleotides were used as competitors (mutated residues are in small case).

Some in vitro translation reactions were done in the presence of radiolabeled [$^{35}$S]-methionine and analyzed by SDS PAGE in 12.5% polyacrylamide. After coumassie staining, the gel was soaked in fluorescent enhancer solution Amplify (Amersham), heat-dried and exposed to Biomax-MR film (Kodak) for 1 hr.

Transfections

Pet-1 effector construct (CGS-Pet-1) was prepared by Xbal/Kpnl subcloning from p73-7Z into pCGS (Monuki et al., 1990). For multimerized wild type and mutant PEA3 binding site luciferase reporters, 3XP$\alpha$3(−238/+47)-luc and 3XPm$\alpha$3(−238/+47)-luc, double-stranded oligonucleotides (40 bp) were cloned upstream of minimal $\alpha$3 promoter by Kpnl/Pmll ligation. The following oligonucleotides were used: 3XP ((CA GGA AGT GAC TCA GGA AGT GAC TCA GGA AGT GAC AC (SEQ ID NO:22), top strand)) and 3XPm ((CA tcA AGT GAC TCA tcA AGT GAC TCA tcA AGT GAC AC (SEQ ID NO:23), top strand)). Cell lines were transfected by electroporation as described (Yang et al., 1994). For all transfections, 10 $\mu$g of a reporter, 5 $\mu$g RSV-$\beta$gal construct and 0–10 $\mu$g effector were used. Total DNA amount was brought to 25 $\mu$g with empty promoter vector (pCGS). Cells were harvested 40 hr post-transfection and lysates were assayed for luciferase and $\beta$-galactosidase activities.

Plasmids

The adenovirus major late promoter (MLP) was introduced into pGL2basic (Promega Corp.) to make MLP-luc. This plasmid was used to prepare reporters that have four copies of different Pet-1 binding sites shown in Table 1 which were placed upstream of the promoter using SacI/XhoI polylinker sites. Synthetic oligonulceotides were obtained from Life Technologies, Inc. All reporters were sequenced through the cloning region to verify sequence of introduced oligonucleotides. CMV-Pet-VP16 was prepared by subcloning into pCGS (11) Pet-1 cDNA sequences encoding amino acids 146–229 upstream of VP16 sequences encoding amino-acids 411–490. The linker sequence between Pet-1 residues and VP16 residues is EFPGI. The SV40 nuclear localization signal is positioned at the amino-terminus of the fusion protein.

Retinal Cell Culture and Transfections

Retinas were dissected from P1 rat pups, and dissociated in 5 mg/ml dispase (Roche) for 5 min. Following a rinse in serum containing medium, retinas were triturated with a fire-polished Pasteur pipet in serum-containing medium with 3.5% bovine serum albumin (Gibco), and plated at ~5×10$^5$ cells per well of PLL-LN coated 24-well plates. Cultures were plated in the same media, but changed to serum free medium after about 24 hours. Serum free medium consisted of DMEM supplemented with Insulin-Transferrin-Selenium (ITS, Sigma), pen-strep, 0.1 mg/ml sodium pyruvate (Sigma), bovine serum albumin (1.5%) and 10 ng/ml recombinant human brain-derived neurotrophic factor (Peprotcch, Rocky Hill, N.J.). Cultures were allowed to grow for 3 days before transfection. Calcium phosphate transfections were performed essentially as described (12). 2 mg of reporter DNA and 1 $\mu$g CMV-Pet-1-VP16 effector were used per transfection for luciferase assays. PC12 cell transfections were performed by electroporation as described (13).

Northern Analysis and RNase Protection

For Northern analysis 10 $\mu$g PC12 total RNA was run on 1.5% agarose formaldehyde gel and transferred to nylon in 10X SSC using standard procedures (Sambrook et al., 1989). A 166 bp XhoI/HindIII fragment (positions 1552–1717) and a 263 bp Rsal fragment (201–463) of $\lambda$73 insert were random prime labeled and used as probes. After hybridization in 50% formamide, 6X SSC, 7X Denhardt's, 1% SDS at 42° C. overnight, the blot was washed at high stringency and exposed for 2 days.

For protection analyses, 10 $\mu$g p73-7Z plasmid was digested with Xho1 and desalted with QIAEX II (Qiagen Inc.) into 20 $\mu$l 10 mM Tris-HCl pH 7.9 (RNase-free). Similarly pTRI-$\beta$Actin (Ambion Inc., Austin, Tex.) was cut with Aoc1. The final concentrations of linear DNA templates were about 0.4 mg/ml. Antisense RNA probes were transcribed by SP6 RNA polymerase (Boehringer-Mannheim) in vitro from 600 ng template in 10 $\mu$l total volume at 37° C. for 1 hr. Nucleotide concentrations were 0.5 mM except for UTP for which 64 $\mu$Ci [$\alpha$-$^{32}$P]-UTP (800 Ci/mmole) were used instead. To reduce specific activity of the $\beta$-actin probe unlabeled UTP was added to the reaction to 0.5 mM. The reactions were heated to 100° C. for 5 min, cooled on ice for 2 min and digested with 10 units DNase I, RNase-free (Boehringer-Mannheim) for 5 min at 37° C. The probe was ethanol precipitated, resuspended in formamide loading buffer, gel purified (6.5% polyacrylamide/8 M urea) and eluted overnight in 0.5 M NH$_4$OAc, 1 mM EDTA, 0.2% SDS. Total RNA was isolated from cell lines and tissues with Qiagen's RNeasy kit. Tissues were frozen in liquid nitrogen and homogenized with mortar and pestle. Twenty micrograms total RNA was used in protection experiments except for PC12 cells protection where 2 $\mu$g were used. RNase protection reactions were carried out with Ambion RPA II kit as recommended by the manufacturer and run on a 6% denaturing polyacrylamide gel. The gels were soaked in 10% methanol/15% acetic acid, heat dried and exposed to X-OMAT-AR film (Kodak) for 3–7 days. Some gels were exposed overnight to a phosphorimager screen (Molecular Dynamics) for quantitation.

In Situ Hybridization p73-7Z was digested with HindIII and religated to delete the poly(A) tail. The resulting plasmid p73$\Delta$A-7Z was digested with EcoN1 and gel purified. An [$^{35}$S] antisense RNA probe was synthesized by in vitro transcription with SP6 RNA polymerase as described above for the protection probe. Animal perfusion, tissue sectioning, and hybridization were performed exactly as described (Simmons, D. M., et al., "A complete protocol for in situ hybridization of messenger RNAs in brain and other tissues with radiolabeled single-stranded RNA probes" *J. Histotech.* 12:169–181, 1989). After posthybridization treatment slides were exposed to Biomax-MR film (Kodak) for three days.
Histology The [35S]-radiolabeled and non-radiolabeled digoxigenin-(DIG) Pet-1-specific antisense RNA probes for in situ hybridization analyses were prepared using as template a 1.0 kb fragment of p73-7Z carrying our full length Pet-1 cDNA (Fyodorov, D., et al., *J. Neurobiol.* 32:151–163, 1998). This portion of the cDNA encodes an unconserved region of the Pet-1 protein beginning at an EcoN1 site just downstream of the ETS domain and continuing through the 3'-untranslated region. Preparation of [35S]-Pet-1 probe and radiolabeled in situ hybridization were performed as described (Deneris, E. S., et al., Neuron 1:45–54, 1988). Radiolabeled hybridization signals from 20–30 µm coronal sections of adult rat brain were obtained on Kodak XAR film exposed at room temperature for 2–3 days. DIG-Pet-1 probes were synthesized with digoxigenin-11-UTP according to manufacturer's instructions (Roche, Mannheim, Germany). Embryos were staged according to Christie (Christie, G. A., *J. Morphol.* 114:263–286, 1962) by a combination of somite counts and crown to rump measurements. Embryos were cryoprotected in 20% sucrose (w/v) in phosphate buffered saline, embedded in OCT (Electron Microscopy Sciences, Ft. Washington, Pa.), and frozen on dry ice. Twenty µm cryosections of adult and embryonic brain were used for DIG-Pet-1 in situ hybridization essentially as described (Schaeren-Weimers, N., and Gerfin, A., Histochemistry 100:431–440, 1993). Slides were washed and developed for 3 hr to 3 days at RT in the dark. For combined DIG-Pet-1 in situ hybridization and anti-tryptophan hydroxylase immunohistochemistry, sections were first hybridized with DIG-Pet-1 probe then stained with a 1:100 dilution of anti-tryptophan hydroxylase monclonal antibody (Sigma) overnight at 4° C. in humidified petri dishes. The next day sections were rinsed in 1× phosphate buffered saline 3 times for 15 min each and then incubated for 1–2 hr at room temperature with 1:100 dilution biotinylated goat anti-rabbit IgG antibody in 1× dilution buffer (2% bovine serum albumin, 0.3% TritonX-100, 0.1% sodium azide, 5% sheep serum in 1× phosphate buffered saline). Horseradish peroxidase reactions were performed using the avidin-biotin-peroxidase complex (Vectastain ABC kit; Vector, Burlingame Calif.). 5-HT immunohistochemistry was performed as described for anti-tryptophan hydroxylase antibody staining with 1:10,000 dilution rabbit anti-5-HT antibody (Incstar, Stillwater Minn.) and the Vectastain ABC procedure.

Electrophoretic Mobility Shift Assay

Pet-1 was expressed in and purified from bacteria and then used for EMSA with approximately 200 ng of Pet-1 and 200–400 molar excess of unlabeled competitors as described (Fyodorov, D., and Deneris, E., *Mol. Cell. Biol.* 16:5004–5014, 1996).

EXAMPLE 1
Pet-1: A Novel Member of the ETS-domain Family of Transcription Factors We analyzed PC12 cells for the presence of ETS-domain transcripts by RT-PCR. Degenerate PCR primers were prepared based on conserved amino-acid sequences (FIG. 1) in various ETS domains and used to amplify reverse transcribed PC12 cell RNA. Analysis of PCR products revealed two classes of ETS-domain sequences. One class comprised of two clones contained sequences that indicated identity to ETS-2 sequences (Watson, D. K., et al., "Mammalian ets-1 and ets-2 genes encode highly conserved proteins" *Proc. Natl. Acad. Sci. USA* 85:7862–7866, 1988). The deduced amino-acid sequences of the second class, comprised of eight clones, are identical to one another. Database comparison indicated an ETS-domain sequence that was most closely related to the ETS-domain of the human and mouse homologues, FLI-1 and ERG (Ben-David, Y., et al., "Erythroleukemia induction by Friend murine leukemis virus: insertional activation of a new member of the ets gene family, Fli-1, closely linked to c-ets-1" *Genes Dev.* 5:908–918, 1991; Shyam, E., et al., "The erg gene: A human gene related to the ets oncogene" *Proc. Natl. Acad. Sci. USA* 84:6131–6135, 1987). There are several non-conservative amino-acid differences, however, between this PC12 cell-derived sequence and ERG/FLI-1 in their ETS-domains, which suggests that PC12 cells may express a novel ETS-domain factor.

To determine the complete primary structure of the novel ETS-domain factor, we screened a PC12 cell plasmid and γgt11 cDNA libraries with the PCR fragment. Fourteen related clones were isolated and characterized by restriction endonuclease mapping. The clone with the longest insert, designated β73, was subcloned and sequenced on both strands. The 1,752 bp cDNA insert of β73 contains a 1,020 nucleotide open reading frame beginning with an ATG at position 112 and ending with a TAG at position 1,132. The λ73 cDNA ends with a long poly(A) tract, which is 12 nucleotides downstream of a potential polyadenylation site (FIG. 1). The partial ETS-domain sequence encoded by the original PCR product is present in roughly the middle of the β73 cDNA open reading frame. Thus the β73 cDNA encodes an ETS-domain protein of 340 amino-acids with a predicted molecular weight of 35.4 kDa (FIG. 1).

Figure 2A:
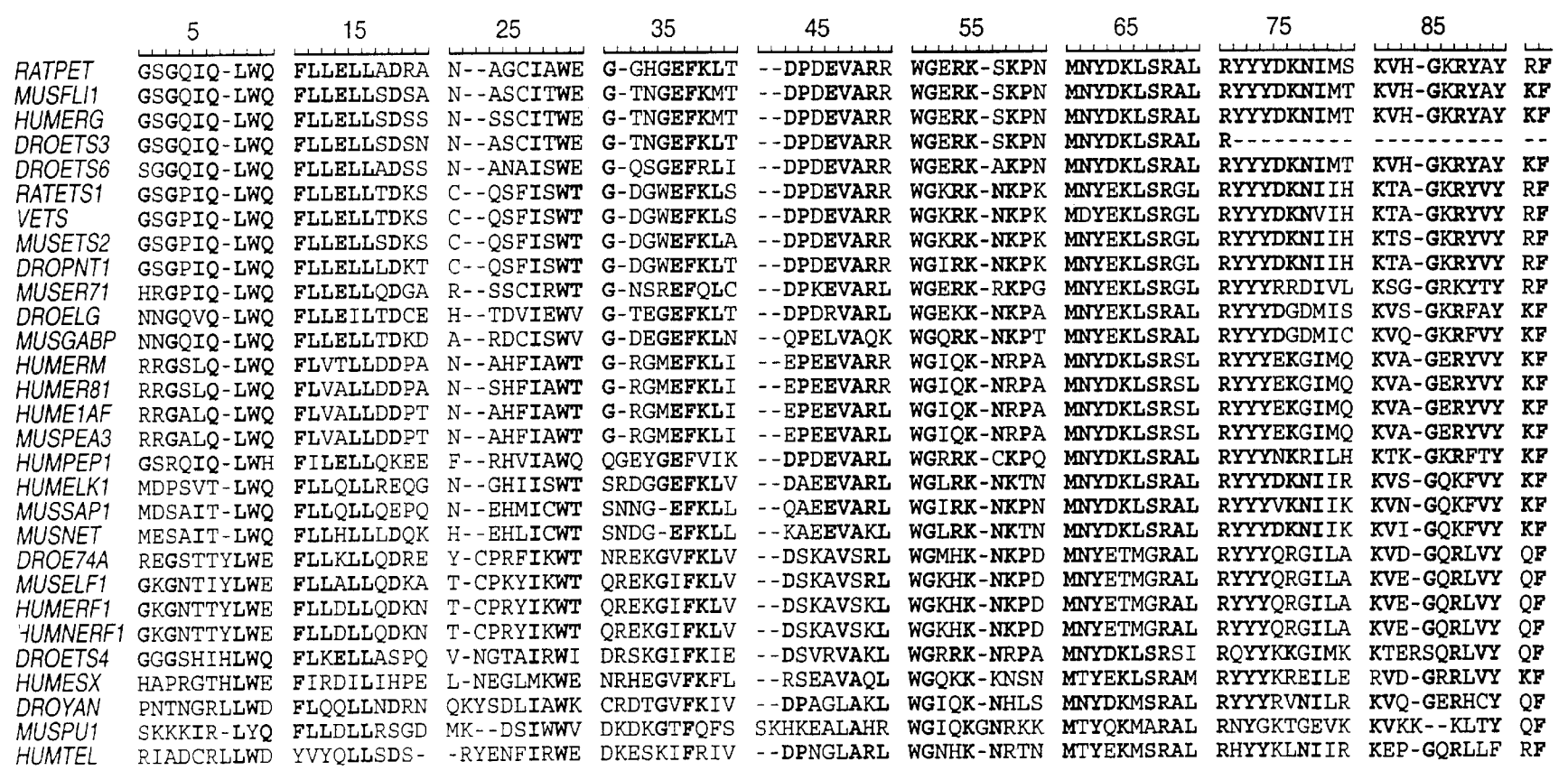
Figure 2B:
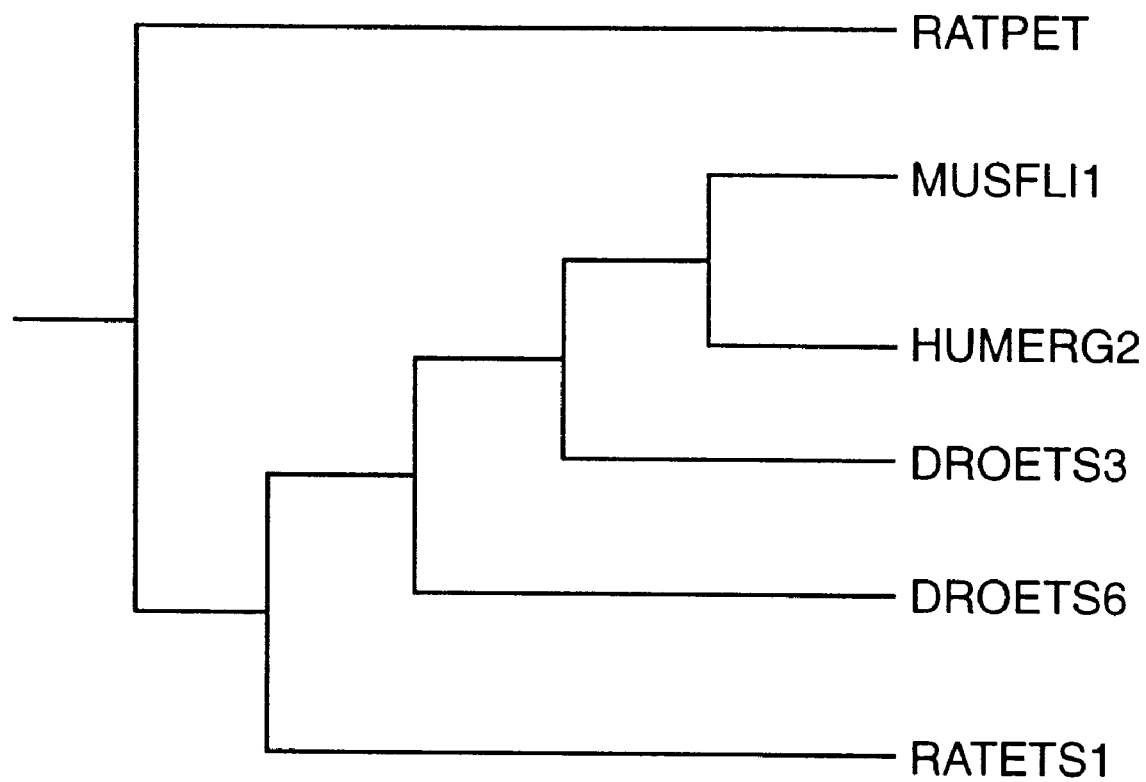
FIG. 2 show the alignment of various ETS-domain sequences. A) The first three letters of each ETS-domain factor designation shown on the left indicate an organism, e.g. DRO, *Drosophila melanogaster*, followed by the common gene name. Columns of more than 40% sequence identity are in bold text. B) Parsimony analysis of sequences encoding different ETS domains. The phylogenetic tree demonstrates relative similarities among the ETS DNA binding domains of Pet-1, Ets-1 and members of the ERG subfamily. The available sequence for the Drosophila ETS-3 ETS domain is incomplete (Chen, T., et al., "Isolation and characterization of five Drosophila genes that encode an ets-related DNA binding domain" *Dev. Biol.* 151:176–191, 1992). Branch lengths do not represent estimates of evolutionary distances between protein sequences.

As described above, the deduced ETS domain amino-acid sequence within the β73 insert is most closely related to the ETS-domains of the ERG sub-family (FIG. 2A), which includes human ERG (87% sequence identity), mouse FLI-1 (89%), and Drosophila ETS-3 (91%, incomplete fly sequence) (Chen, T., et al., "Isolation and characterization of five Drosophila genes that encode an ets-related DNA binding domain" *Dev. Biol.* 151:176–191, 1992) and ETS-6 (86%) (Chen, T., et al., "Isolation and characterization of five Drosophila genes that encode an ets-related DNA binding domain" *Dev. Biol.* 151:176–191, 1992). Outside the ETS domain, however, the protein encoded by sequences in the β73 insert bears no significant sequence identity with other members of the ETS family of transcription factors. This indicates that the β73 insert encodes a novel ETS-domain protein that we have named Pet-1, PC12 ets factor. Parsimony analysis of the Pet-1 ETS domain suggests that Pet-1 may represent a distinct subfamily of ETS-domain proteins (FIG. 2B).

Figure 3:
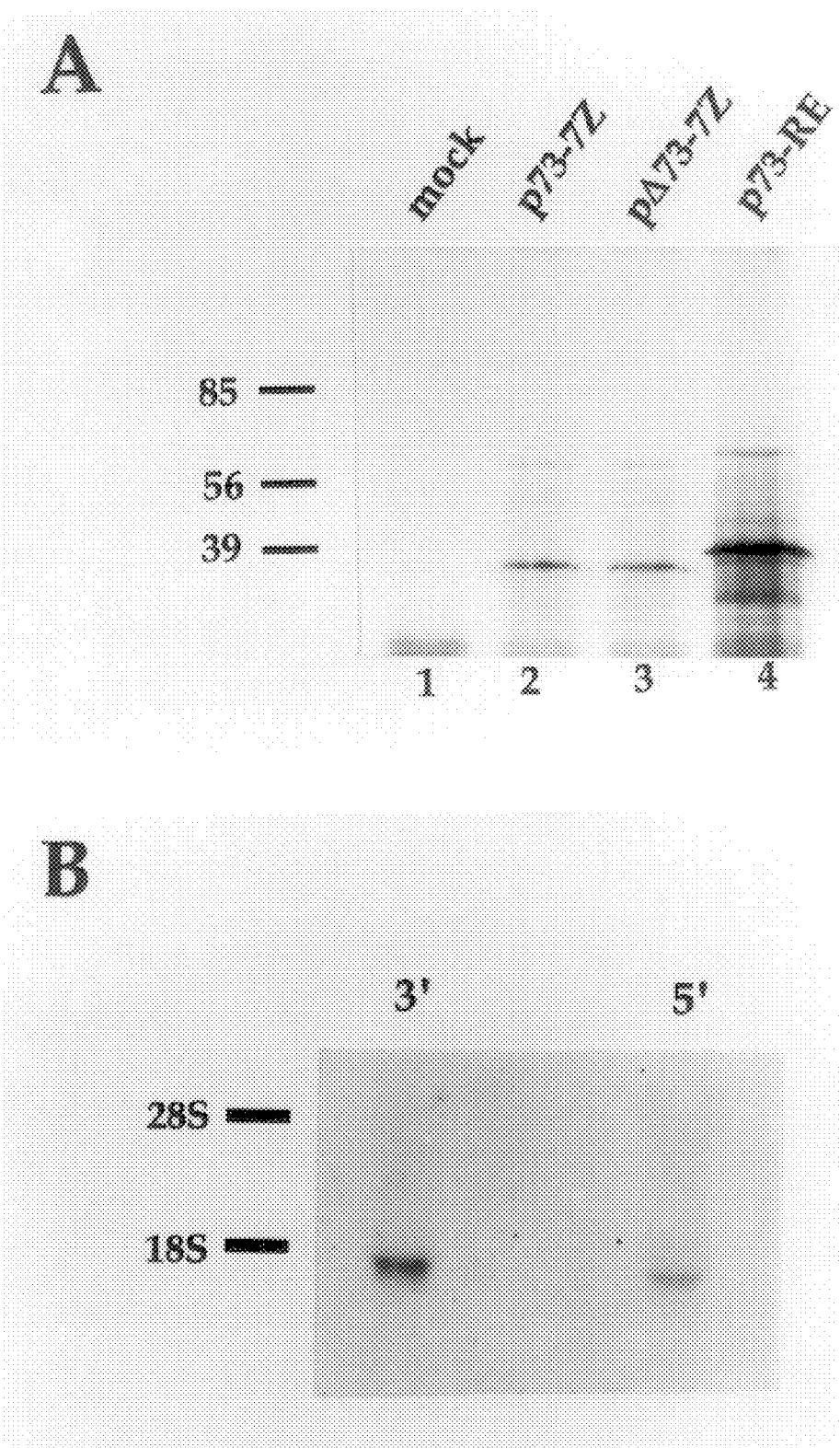
FIG. 3 shows the analyses of the λ73 cDNA. A) In vitro translation of λ73 cDNA templates. cDNA templates encoding Pet-1 and EE-tagged Pet-1 polypeptides (Experimental Procedures) were used in a coupled T7 in vitro transcription/translation system. The products were radiolabeled by [$^{35}$S]-methionine incorporation, fractionated on SDS-PAGE followed by autoradiography. The position of the molecular weight (kDa) standards are shown on the left. Lane 1, no template; lane 2, p73-7Z template containing the full length λ73 cDNA; lane 3, pΔ73-7Z template lacking upstream ATG triplets; lane 4, p73-RE template containing λ73 cDNA modified to encode an EE-epitope tag. B) Northern analysis of PC12 cell Pet-1 transcripts. PC12 cell total RNA was hybridized to probes made with fragments from either the 3' end (left) or 5' end (right) of λ73.

The putative initiator methionine codon at position 112 is preceded immediately by an in-frame TAG stop codon. The assigned initiator codon is positioned in a good but not optimal context for translation (G in position +4, but no purine in position −3, (Kozak, M., "Structural features in eukaryotic mRNAs that modulate the initiation of translation" *J. Biol. Chem.* 266:19867–19870, 1991) and weak secondary structure formation is possible just upstream. Further upstream are three other ATG triplets one of which, at position 77, is out of frame with the assigned initiator methionine codon. This latter triplet, which is positioned in a poor context for translation, begins an open reading frame that ends at nucleotide position 216. This reading frame overlaps with the frame encoding the predicted ETS-domain protein and has the potential to encode a 13 kDa polypeptide. We investigated our assigned ETS-domain protein open reading frame by translating the β73 cDNA, in vitro. In one reaction, a plasmid (p73-7Z) containing the full-length β73 cDNA was placed downstream of the T7 promoter. This construct has the capacity to initiate translation at one or both of the possible initiator methionine codons. In a separate reaction, a plasmid (pΔ73-7Z) containing the β73 cDNA that was truncated upstream of position 108 was used for in vitro translation. This construct contains only the assigned ETS-domain protein initiator methionine codon. Coupled in vitro transcription/translation of each template in rabbit reticulocyte lysate produced proteins indistinguishable in size and both with an apparent molecular weight of about 38 kDa (FIG. 3A, lanes 2 versus 3). This result supports our assigned boundaries for the ETS-domain open reading frame. The significance of the upstream overlapping reading frame is not clear, but it could be involved in translational regulation of Pet-1.

To determine the size of Pet-1 transcripts in PC12 cells, we performed northern analysis using total RNA. Restriction fragment-derived probes from either the 5' or 3' ends of the β73 insert detected a single band of 1.7 kb (FIG. 3B). This result indicates that clone β73 contains most or all Pet-1 exon sequences expressed in PC12 cells.

EXAMPLE 2

Features of the Pet-1 Deduced Primary Structure

The Pet-1 ETS domain is positioned in the middle of the polypeptide and is flanked by a proline-rich (21%) and serine-rich (10%) amino-terminal domain and a proline-rich (14.5%) and alanine-rich (33%) carboxy-terminal domain (FIG. 1). A 12 residue-long alanine string is present in the carboxy-terminal domain. Proline-rich regions are suggestive of transcriptional activation domains (Mitchell, P. J., and Tjian, R., "Transcriptional regulation in mammalian cells by sequence-specific DNA binding proteins" Science 245:371–378, 1989), but have also been implicated in repression (Han, K., and Manley, J. L., "Transcriptional repression by the Drosophila Even-skipped protein: definition of a minimal repression domain" Genes. Dev. 7:491–503, 1993). Similarly, alanine-rich domains, including long uninterrupted alanine strings, are found in many transcription factors, including several ETS-domain factors, and have been shown in some instances to be important for transcriptional repression (Han, K., and Manley, J. L., "Transcriptional repression by the Drosophila Even-skipped protein: definition of a minimal repression domain" Genes. Dev. 7:491–503, 1993). However, deletion of an alanine string in the amino-terminal activation domain of the POU factor SCIP had no effect on the activity of this factor (Monuki, E. S., et al., "Cell-specific action and mutable structure of a transcription factor effector domain" Proc. Natl. Acad. Sci. USA 90:9978–9982, 1993). There are no other regions immediately apparent that are rich in particular amino-acids such as acidic ones or glutamine that would be suggestive of other kinds of transcriptional activation domains (Mitchell, P. J., and Tjian, R., "Transcriptional regulation in mammalian cells by sequence-specific DNA binding proteins" Science 245:371–378, 1989). Present on the amino-terminal side of the ETS-domain are several MAP kinase consensus phosphorylation sites, two of which match the optimal PX(S/T)P consensus site (FIG. 1) (Clark-Lewis, I., S, et al., "Definition of a consenus sequence for peptide substrate recognition by p44mpk, the meiosis-activated myelin basic protein kinase" J. Biol. Chem. 266:15180–15184, 1991; Haycock, J. W., et al., "ERK1 and ERK2, two microtubule-associated protein 2 kinases, mediate the phosphorylation of tyrosine hydroxylase at serine-31 in situ" Proc. Natl. Acad. Sci. USA 89:2365–2369, 1992).

Several ETS-domain factors, such as Elk-1, ERF, Pointed, and Yan, have been shown to be targets of Ras/MAP kinase signal transduction pathway (Brunner, D., et al., "The ETS domain protein Pointed-P2 is a target of MAP kinase in the Sevenless signal transduction pathway" Nature 370:386–389, 1994; Marais, R., et al., "The SRF accessory protein Elk-1 contains a growth factor-regulated transcriptional activation domain" Cell 73:381–393, 1993; O'Neill, E. M., et al., "The activities of two Ets-related transcription factors required for Drosophila eye development are modulated by the Ras/MAPK pathway" Cell 78:137–147, 1994; Sgouras, D. N., et al., "ERF: an ETS domain protein with strong transcriptional repressor activity, can suppress ets-associated tumorigenesis and is regulated by phosphorylation during cell cycle and mitogenic stimulation" EMBO J. 14:4781–4793, 1995). The presence of several consensus Ras/MAP kinase phosphorylation sites in the Pet-1 amino-terminal region suggests Pet-1 may also be a nuclear target of this signal transduction cascade. A consensus phosphate-binding loop (P-loop) GXXXXGKS motif is also present 12 amino acids upstream of the Pet-1 ETS domain (Saraste, M., et al., "The P-loop-a common motif in ATP- and GTP-binding proteins. Trends Biochem. Sci. 15:430–434, 1990).

EXAMPLE 3

Pet-1 RNA Expression Pattern

Figure 4:
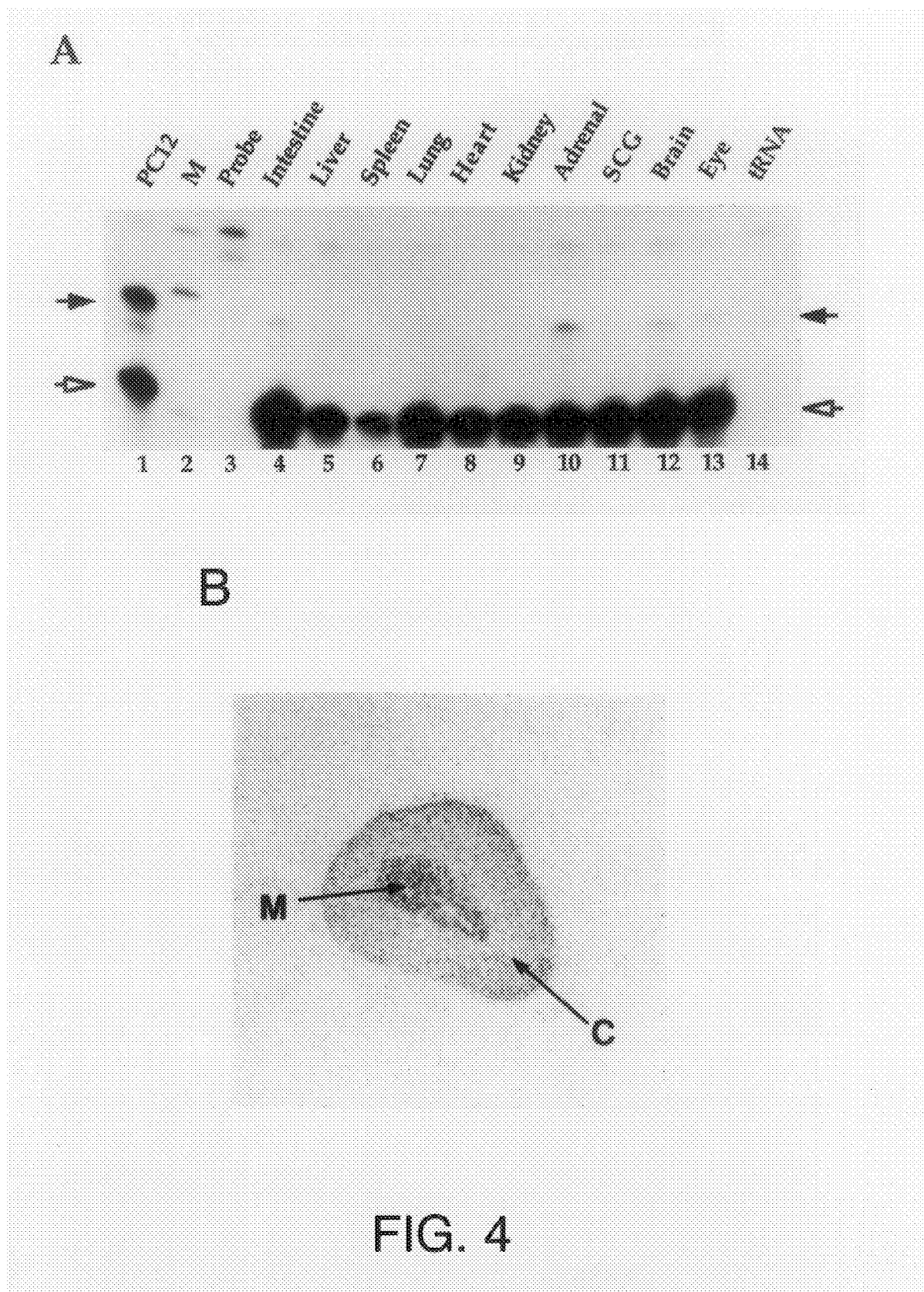
FIG. 4 shows the tissue distribution of Pet-1 RNA. A) RNase protection analysis of Pet-1 transcripts in rat tissues. Two µg PC12 total RNA (lane 1) or 20 µg total RNA isolated from the indicated P0 tissues (lanes 4–13) were analyzed by RNase protection using Pet-1 and β-actin specific probes. Lane 14, yeast transfer RNA as a negative control. Lane 2, radiolabeled DNA molecular weight markers (pGEM, Promega Corp.) of sizes 222, 179 and 126bp. Closed arrows indicate Pet-1 protected product. Open arrows indicate β-actin protected product. B) Expression of Pet-1 gene in the adrenal medulla. M, adrenal medulla; C, adrenal cortex. Sections were hybridized to a Pet-1-specific [$^{35}$S]-antisense RNA probe as described in the Experimental Procedures.

We used a combination of RNase protection analyses and in situ hybridization with probes made from non-conserved regions flanking the ETS-domain to determine the pattern of Pet-1 expression. We first analyzed by RNase protection the distribution of Pet-1 RNA in various mammalian cell lines. Of all cell lines tested (PC12, rat pheochromocytoma; C6, rat CNS glioma; C1300, mouse neuroblastoma; Rat2, rat fibroblast; Clone 9, rat normal liver; ARIP, rat pancreatic tumor; and HeLa, human cervical carcinoma) only the neuroendocrine PC12 line expresses detectable amounts of Pct-1 RNA (data not shown), which suggested that Pet-1 has a restricted pattern of expression in vivo. To investigate this, we analyzed total RNA from various rat tissues for Pet-1 expression by RNase protection (FIG. 4A). As expected from the high levels of Pet-1 RNA detected in PC12 cells, strong Pet-1 gene expression was detected in the adrenal gland. Lower levels of Pet-1 RNA expression were also detected in brain, small intestine and eye. No expression was detected in liver, spleen, lung, heart, kidney, superior cervical ganglia, and thymus. In situ hybridization showed that Pet-1 is expressed in the adrenal medulla, which is consistent with expression of Pet-1 in the adrenal medullary tumor-derived PC12 line (FIG. 4B).

EXAMPLE 4

Functional Characterization of Pet-1

Figure 5:
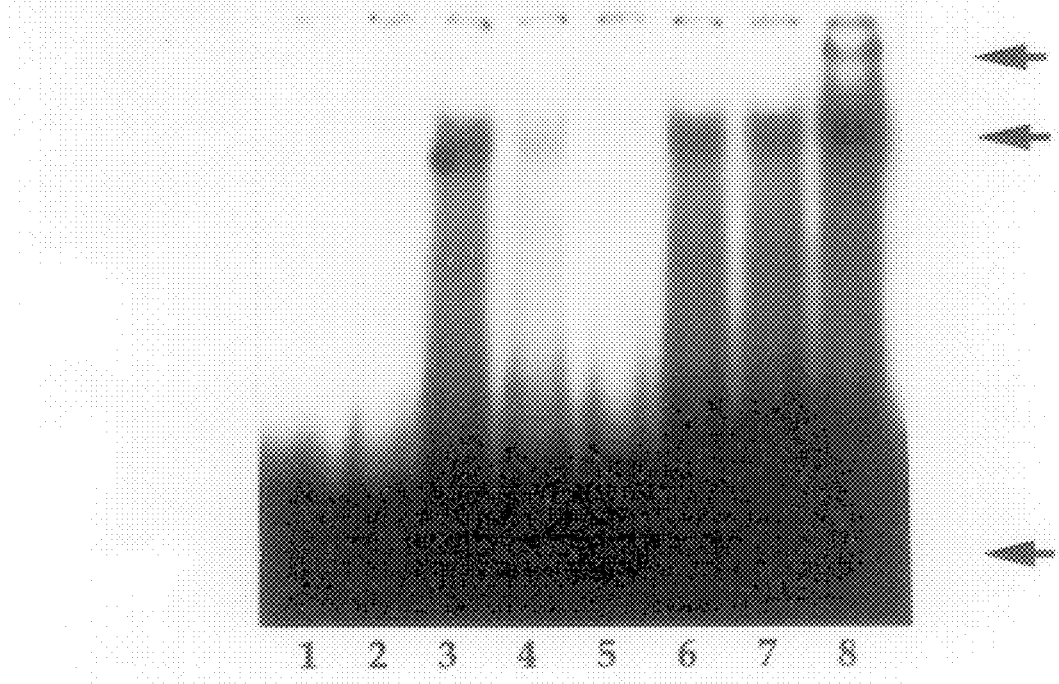

Although the primary structure of Pet-1 strongly suggests that it functions as a transcription factor, we investigated this biochemically by determining whether Pet-1 can bind DNA in a sequence-specific manner and whether it can modulate transcription in an ETS binding site-dependent manner. To determine whether Pet-1 is capable of binding specifically to an ETS DNA binding motif, we performed a mobility shift assay with EE-epitope tagged Pet-1 (EE-Pet-1) translated in vitro (FIG. 3A, lane 4). Binding reactions were performed with a radiolabeled oligonucleotide containing a single PEA3 ETS-domain binding site (Xin, J.-H., et al., "Molecular cloning and characterization of PEA3, a new member of the Ets oncogene family that is differentially expressed in mouse embryonic cells" Genes Dev. 6:481–496, 1992). As shown in FIG. 5, binding reactions with EE-Pet-1 protein and radiolabeled probe resulted in the formation of a single complex that was eliminated by competition with unlabeled wild type oligonucleotide but not with an equivalent amount of oligonucleotide in which the PEA3 DNA binding motif was destroyed. Binding reactions performed in the presence of anti-EE-epitope monoclonal antibody (Yan, M., and Templeton, D. J., "Identification of 2 serine residues of MEK-1 that are differentially phosphorylated during activation by raf and MEK kinase" *J Biol. Chem.* 269:19067–19073, 1994) resulted in a supershifted complex, which confirms that the complexes formed with programmed reticulolysate reactions contain EE-Pet-1 protein (FIG. 5, lane 8). No supershifted complex was detected in a similar experiment with the unprogrammed lysate (data not shown). These results show that the β73 insert encodes an ETS-domain binding protein.

To determine whether Pet-1 can functionally interact with PEA3 sites, we tested Pet-1 in co-transfection assays using a Pet-1 effector construct, CGS-Pet-1, controlled by the cytomegalovirus promoter (Monuki, E., et al., "Expression and activity of the POU transcription factor SCIP" *Science* 249:1300–1303, 1990). As shown in FIG. 6, an α3 minimal romoter (Yang, X., et al., "Characterization of an acetylcholine receptor alpha 3 gene promoter and its activation by the POU domain factor SCIP/Tst-1" *J Biol Chem.* 269:10252–10264, 1994) luciferase reporter containing three upstream PEA3 binding motifs was repressed in a dose-dependent manner by co-transfected CGS-Pet-1. Repression by CGS-Pet-1 was dependent on the presence of intact PEA3 sites, because no repression was seen with the α3 minimal promoter construct bearing mutated PEA3 binding sites. These results demonstrate that Pet-1 can modulate transcription in an ETS binding site-specific manner.

EXAMPLE 5
Pet-1 Can Activate the β43' Enhancer in a Cell-type Specific Manner

As described above, consensus ETS factor binding sites are present in each of the β43' enhancer 37 bp direct repeats. When the GGA core residues (Wasylyk, B., et al., "The Ets family of transcription factors" *Eur. J. Biochem.* 211:7–18, 1993) of these consensus sites are mutated, β43' activity is virtually eliminated. Because the Pet-1 gene is strongly expressed in PC12 cells and adrenal medulla this factor is a candidate for an endogenous ETS-domain factor that regulates neuronal nAchR gene transcription through an interaction with the β43' enhancer. To begin to test this possibility, we performed co-transfections with the CGS-Pet-1 effector and α3 minimal promoter (Yang, X., et al., "Characterization of an acetylcholine receptor alpha 3 gene promoter and its activation by the POU domain factor SCIP/Tst-1" *J Biol Chem.* 269:10252–10264, 1994) reporters bearing one or more copies of the enhancer. As shown in FIG. 7, Pet-1 expression in C6 cells resulted in a modest but reproducible stimulation of reporter activity. Activation occurred in a CGS-Pet-1 dose-dependent and enhancer copy number-dependent manner. Activation was not seen with a reporter carrying mutations in each of the consensus ETS sites in β43' (data not shown). To determine whether other cell types would support activation of β43' by Pet-1, we tested several other lines in co-transfection assays. Activation was not seen in any of the other cell lines tested (FIG. 7). These results suggest that Pet-1 activation requires interaction with additional cell-type specific factors.

EXAMPLE 6
Expression of the Pet-1 Gene in the Central 5-HT system

In situ hybridization was used to determine the spatial distribution of Pet-1 RNA in rat brain. Pet-1 RNA was detected in a small number of scattered midline nuclei in the midbrain/hindbrain region, which correspond to the B1–B9 groups of the midline raphe nuclei (B1, B2, B4–B8) and their lateral extensions (B3, B9) (FIG. 8). No other sites of Pet-1 expression could be identified in brain or spinal cord. Serotonergic neurons within the B1–B9 groups are intermingled with a substantial number of non-serotonergic neurons and glia (Jacobs, B. L., and Azmitia, E. C., *Physiological Reviews* 72:165–220, 1992). To determine whether Pet-1 gene expression is limited to serotonergic neurons in raphe nuclei we compared Pet-1 RNA distribution to 5-HT immunoreactivity on adjacent sections in the region of the midbrain dorsal (B7) and median (B8) raphe nuclei. The general distribution of Pet-1 RNA in the dorsal and median raphe nuclei is strikingly similar to that of 5-HT immunorcactivity (FIGS. 9A, B). For example, clear clustering of Pet-1 RNA is evident in the median raphe as well the dorsal, ventral, and lateral serotonergic neuron fields of the dorsal raphe. Pet-1 RNA was not detected outside of these fields. To confirm colocalization of Pet-1 RNA to serotonergic neurons, we combined Pet-1 in situ hybridization with immunohistochemistry for tryptophan hydroxylase (TPH), the rate-limiting enzyme for 5-HT biosynthesis, on single sections. Pet-1 colocalizes with virtually all TPH-positive neurons in the dorsal raphe nucleus as well as with isolated TPH-positive neurons located more laterally in the central gray (FIGS. 9C, D).

EXAMPLE 7
Pet-1 Expression in the Developing Hindbrain

To determine whether Pet-1 might function in the development of central 5-HT system we investigated its pattern and onset of expression in the embryonic brain. In the developing brain, the 5-HT system is parceled into two subdivisions called the rostral (superior) and caudal (inferior) clusters (Wallace, J. A., and Lauder, J. M., *Brain Res. Bull.* 10:459–479., 1983; Lidov, H. G. W., and Molliver, M. E., *Brain Res. Bull.* 9:559–604, 1982; Aitken, A. R., and Tork, I., *J Comp. Neurol.* 274:32–47, 1988). Both clusters extend longitudinally on either side of the floor plate along the ventral aspect of the neural tube. The developing rostral cluster gives rise to 5-HT neurons comprising B4–B9) groups. These groups provide the majority of ascending serotonergic fibers to the forebrain. The caudal cluster generates 5-HT neurons that will become the B1–B3 groups. These groups constitute the major descending 5-HT projection to the spinal cord. The rostral cluster appears first, showing 5-HT immunoreactivity in the rhombencephalon caudal to the mesencephalic flexure at embryonic day 13 (FIG. 10F) (Wallace, J. A., and Lauder, J. M., *Brain Res. Bull.* 10:459–479, 1983; Aitken, A. R., and Tork, I., *J Comp. Neurol.* 274:32–47, 1988). The caudal cluster of 5-HT neurons appears at least one day later and is located in the myelencephalon, caudal to the pontine flexure (FIG. 10K) (Wallace, J. A., and Lauder, J. M., *Brain Res. Bull.* 10:459–479, 1983; Lidov, H. G. W., and Molliver, M. E., *Brain Res Bull.* 9:559–604, 1982; Aitken, A. R., and Tork, I., *J Comp. Neurol.* 274:32–47, 1988).

Significantly, in E14.0 sagittal sections, two longitudinal domains of Pet-1 expression were detected; one beginning just caudal to the mesencephalic flexure and extending to the apex of the pontine flexure and the other caudal to the pontine flexure (FIG. 10A). In transverse sections through the rostral cluster Pet-1 expression at E14.0 occurs adjacent to the floor plate primarily at the outer boundary of the ventricular zone although some expression is detected within the mantle zone (FIG. 10B). This domain of Pet-1 expression corresponds to the location of the rostral 5-HT neuron cluster at E14.0 (Wallace, J. A., and Lauder, J. M., *Brain Res Bull.* 10:459–479, 1983; Lidov, H. G. W., and Molliver, M. E., *Brain Res Bull.* 9:559–604, 1982).

The temporal relationship between Pet-1 expression and the appearance of 5-HT was then determined in developing brains. The earliest age at which Pet-1 expression could be detected was E12.5 when a small number of isolated Pet-1 positive cells were seen just caudal to the mesencephalic flexure within the ventricular zone (data not shown); at E12.75 significantly greater numbers of Pet-1-positive cells were seen at the outer boundary of the ventricular zone (FIG. 10C). By E13.0, Pet-1 RNA expression on sagittal sections appears as a longitudinal band caudal to the mesencephalic flexure (FIG. 10D, E) and the first 5-HT positive cells were now evident in this region (FIG. 10F). At this age, neither Pet-1 nor 5-HT could be detected in the area caudal to the pontine flexure. By E13.5, the rostral expression domain of Pet-1 has expanded and is now accompanied by a second longitudinal band caudal to the pontine flexure (FIG. 10G). The caudal Pet-1 expression domain is fully developed by E14.0, however, at this age 5-HT immunoreactivity is only beginning to form a longitudinal band in this region (FIG. 10 compare K, J). 5-HT immunoreactivity is not fully developed in the caudal cluster until about E15.5 (FIG. 10L). These data show that similar to the appearance of 5-HT, Pet-1 expression occurs at two different stages in two spatially distinct domains in the developing hindbrain. The two Pet-1 domains correspond to the location of the developing rostral and caudal 5-HT neuron clusters. In each cluster, however, the onset of Pet-1 expression precedes the appearance of 5-HT by about 0.5 days. At these ages, Pet-1 expression was not detected anywhere else in the embryo except for the intestine (data not shown).

EXAMPLE 8
Identification of a Conserved Pet-1 Binding Site in Serotonergic Genes The specific expression pattern of Pet-1 in the developing hindbrain beginning before the appearance of 5-HT and continuing in the adult suggests that Pet-1 functions to establish and maintain the serotonergic phenotype. This led us to investigate whether Pet-1 might directly interact with the regulatory regions of genes whose expression is characteristic of the serotonergic phenotype. To test this idea, we searched for Pet-1 binding sites in or near the promoter regions of serotonergic-specific genes. ETS domain factors bind to sequences containing a GGAA/T core. However, specific sequences spanning several positions on either side of this core motif are obligatory for binding and discrimination among various members of the ETS domain family (Wasylyk, B., et al., *Eur. J. Biochem.* 211:7–18, , 1993). We had shown previously that Pet-1 can bind to a PEA3 ETS binding site (Fyodorov, D., et al., *J. Neurobiol.* 32:151–163, 1998; Martin, M. E., et al., *Proc. Natl. Acad. Sci., USA* 85:5839–5843, 1988) and therefore we used this sequence as the basis for our search. At least one PEA3-like sequence was identified within 2.5 kb from the transcription start sites of both the human and mouse 5-HT1a receptor (Parks, C. L., and Shenk, T., *J. Biol. Chem.* 271:4417–4430, 1996), serotonin transporter (5-HTT) (Heils, A., et al., *J. Neurochem.* 70:932–939, 1998; Mortensen, O. V., Mol. Brain. Res. 68:141–148, 1999), and TPH genes (Boularand, S., *J. Biol. Chem.* 270:3757–3764, 1995; Stoll, J., and Goldman, D., *J. Neurosci. Res.* 28,:57–465, 1991). Additionally, a PEA3-like sequence was found in the large first intron of the human aromatic amino-acid decarboxylase (AADC), which encodes an enzyme required for 5-HT synthesis (Table 1). Each of these sites bound to Pet-1 in mobility shift assays (FIG. 11). The specificity of binding was established by showing that incubation of a molar excess of unlabeled PEA3 oligonucleotides could eliminate complex formation between each of the probes and Pet-1 but not by incubation with altered oligonucleotides in which ETS factors interactions are prevented (FIG. 11) (Wasylyk, B., Eur. *J. Biochem.* 211:7–18, 1993). The human and mouse sequences that bound Pet-1 are highly related to one another and comparison among these sites as well as to those sites that did not show significant Pet-1 binding (data not shown) establishes a tentative Pet-1 consensus binding site for serotonergic genes (Table 1).

Figure 12A:
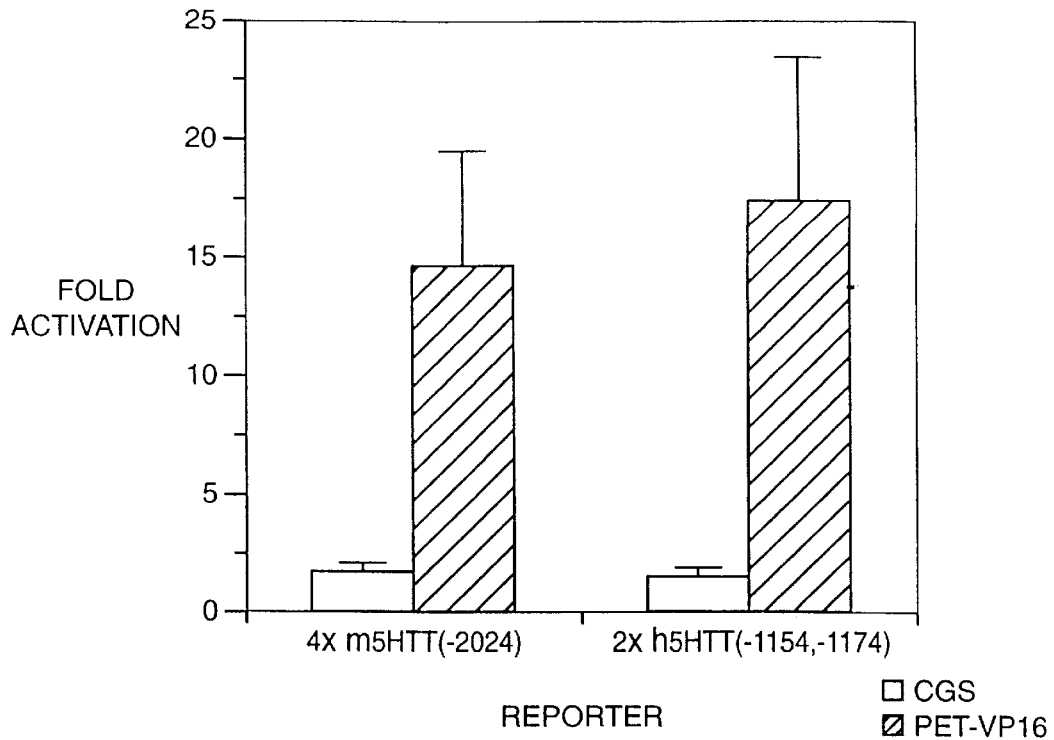
Figure 12B:
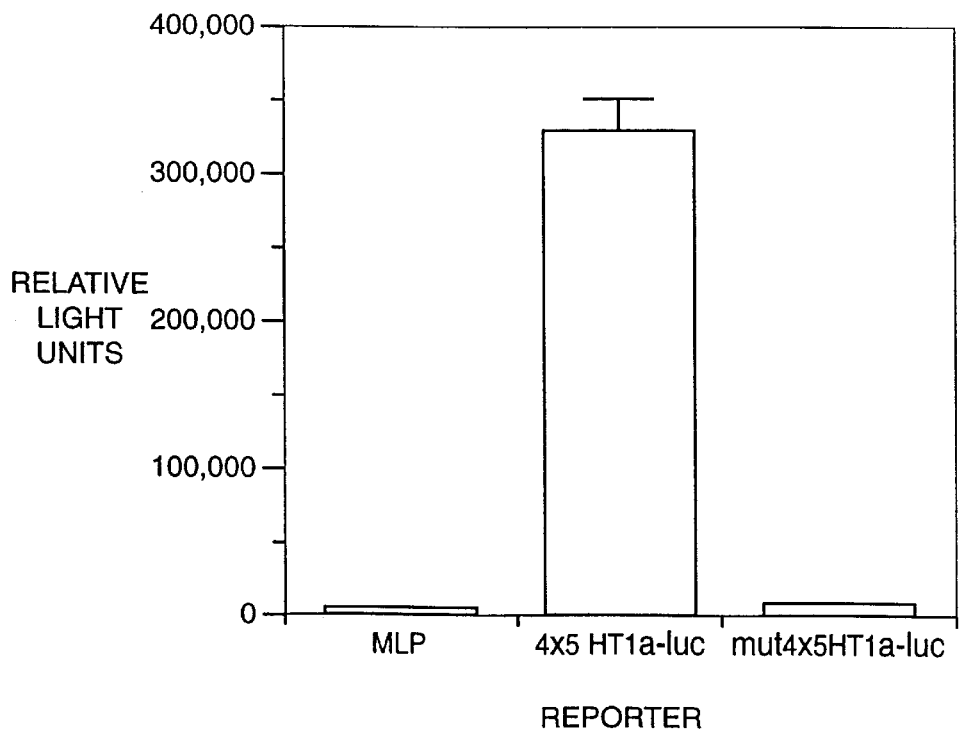

To determine whether Pet-1 binding observed by mobility shift assay is sufficient to modulate transcription in CNS cells we performed transient co-transfections assays in dissociated retinal cultures (Xia, Z., *J. Neurosci.* 16:5425–5436, 1996). Minimal promoter reporters carrying multimerized Pet-1 binding sites found in the upstream region of mouse and human 5-HTT genes were transfected along with an effector plasmid constructed to express the Pet-1 DNA binding domain fused to the herpes simplex virus VP16 activation domain. The VP16 activation domain was used in place of the relatively weak Pet-1 activation domain (Fyodorov, D., et al., *J. Neurobiol.* 32:151–163, 1998). The chimeric effector stimulated reporter gene expression in a Pet-1 binding site-dependent manner (FIG. 12A). These findings demonstrate that the interaction of the Pet-1 DNA binding domain with 5-HTT Pet-1 binding sites can support transcriptional activation. To test whether these sites are capable of stimulating basal transcription, we assayed the activity of reporter plasmids in which four copies of the human 5-HT1a receptor Pet-1 binding site (Table 1) were placed upstream of a minimal promoter. PC12 cells were chosen for this experiment because these cells express high levels of Pet-1 (Fyodorov, D., et al., *J. Neurobiol.* 32:151–163, 1998). Reporter expression was stimulated greater than 200-fold in plasmids carrying multimerized Pet-1 binding sites relative to the minimal promoter alone, but no enhancement of the promoter was seen when the GGA core of each Pet-1 binding site was mutated (FIG. 12B). These results demonstrate that the 5-HT1a receptor Pet-1 binding site can function as autonomous enhancer element in PC12 cells.

From the forgoing, it should be evident that the present invention provides reagents and methods for the screening of compounds that are agonistic or antagonistic to seronergic receptor activity.

What is claimed is:

1. An isolated and purified oligonucleotide having a sequence selected from the group consisting of SEQ ID NOs: 6, 7, 8, 9, 10, 11, or 12.

2. A complex, comprising a purified peptide encoded by the nucleic acid of SEQ ID NO:1, said peptide bound to DNA, said DNA having a sequence selected from SEQ ID NOs: 3, 4, 5, 6, 7, 8, 9, 10, 11 or 12.

* * * * *

SEQUENCE LISTING

<160> NUMBER OF SEQ ID NOS: 23

<210> SEQ ID NO 1

-continued

```
<211> LENGTH: 1752
<212> TYPE: DNA
<213> ORGANISM: Rattus norvegicus
<220> FEATURE:
<221> NAME/KEY: CDS
<222> LOCATION: (112)..(1131)

<400> SEQUENCE: 1
```

| | |
|---|---:|
| tttgttttaa caaacatgtt tattagaaaa gtaaaaatat tgcataggtc ttagtacttg | 60 |
| aacatcaagt gtattcatga accgtgagta tcttcatgta aacagttcta g atg gaa<br>                                                                                                       Met Glu<br>                                                                                                             1 | 117 |
| gac cca ggt ggc gct cct ctg ggg gag agg gtt cca gcc ccc cac ccc<br>Asp Pro Gly Gly Ala Pro Leu Gly Glu Arg Val Pro Ala Pro His Pro<br>              5                        10                          15 | 165 |
| cct cag ccc cat ccc ctc aca gct cac tcc tcc agt aca ccg gca ccg<br>Pro Gln Pro His Pro Leu Thr Ala His Ser Ser Ser Thr Pro Ala Pro<br>    20                        25                          30 | 213 |
| gga tgg gct ggg atg cag ctc cag gac ccc ctc cct cct cac cac acc<br>Gly Trp Ala Gly Met Gln Leu Gln Asp Pro Leu Pro Pro His His Thr<br> 35                     40                          45                        50 | 261 |
| ctg gct gcc cgc tcc cgc cag gcc ttg ccg gac ccg gcg gcg tct act<br>Leu Ala Ala Arg Ser Arg Gln Ala Leu Pro Asp Pro Ala Ala Ser Thr<br>                        55                          60                        65 | 309 |
| ctt ccc tgt cac cca cag tca cca cgg gcg ggt atc ggc acc cca agc<br>Leu Pro Cys His Pro Gln Ser Pro Arg Ala Gly Ile Gly Thr Pro Ser<br>              70                        75                          80 | 357 |
| gca aag ctg acg tgc ccc ccc gtg cgg tcc ccc cca tct ccc acc gcc<br>Ala Lys Leu Thr Cys Pro Pro Val Arg Ser Pro Pro Ser Pro Thr Ala<br>             85                        90                        95 | 405 |
| cag tcc ccg gca gcg atg aga cag agc ggc acc tcc cag ccc ctg ctg<br>Gln Ser Pro Ala Ala Met Arg Gln Ser Gly Thr Ser Gln Pro Leu Leu<br>100                     105                         110 | 453 |
| atc aac atg tac cta cca gat ccc gtc gga gat ggt ctt ttt aag gaa<br>Ile Asn Met Tyr Leu Pro Asp Pro Val Gly Asp Gly Leu Phe Lys Glu<br>115                   120                     125                     130 | 501 |
| ggg aag agc ccg agc tgg ggg ccg ctg agc cct gcg gta cag aaa ggc<br>Gly Lys Ser Pro Ser Trp Gly Pro Leu Ser Pro Ala Val Gln Lys Gly<br>                     135                     140                     145 | 549 |
| agc ggg cag atc cag ttg tgg cag ttt cta ctg gag ctg ctg gca gac<br>Ser Gly Gln Ile Gln Leu Trp Gln Phe Leu Leu Glu Leu Leu Ala Asp<br>                 150                     155                     160 | 597 |
| cgc gcg aac gcc ggc tgc atc gcg tgg gag ggc ggc cac ggc gag ttc<br>Arg Ala Asn Ala Gly Cys Ile Ala Trp Glu Gly Gly His Gly Glu Phe<br>            165                     170                     175 | 645 |
| aag ctc acc gac ccc gac gag gtg gcg cga cgt tgg ggc gag cgc aag<br>Lys Leu Thr Asp Pro Asp Glu Val Ala Arg Arg Trp Gly Glu Arg Lys<br>180                   185                     190 | 693 |
| agc aag ccc aat atg aac tac gac aag cta agt cga gca ctg cgc tac<br>Ser Lys Pro Asn Met Asn Tyr Asp Lys Leu Ser Arg Ala Leu Arg Tyr<br>195                   200                     205                     210 | 741 |
| tac tac gac aaa aac atc atg agc aag gtg cac ggc aag cgc tac gcc<br>Tyr Tyr Asp Lys Asn Ile Met Ser Lys Val His Gly Lys Arg Tyr Ala<br>                     215                     220                     225 | 789 |
| tac cgc ttt gac ttc cag ggc ctg gca cag gct tgc cag cca cca ccc<br>Tyr Arg Phe Asp Phe Gln Gly Leu Ala Gln Ala Cys Gln Pro Pro Pro<br>                     230                     235                     240 | 837 |
| gcg cac gcc cac gcc gcc gct gcc gcc gcc gca gcg gca gcc gcc gcc<br>Ala His Ala His Ala Ala Ala Ala Ala Ala Ala Ala Ala Ala Ala Ala<br>              245                        250                        255 | 885 |

```
cag gat ggc gca ctt tac aag ctc ccg gct ggt ctg gct cca ctg ccc      933
Gln Asp Gly Ala Leu Tyr Lys Leu Pro Ala Gly Leu Ala Pro Leu Pro
    260                 265                 270 ttc ccc ggc ctc tcc aaa ctc aac ctt atg gca gcc tcg gcc ggc gtg      981
Phe Pro Gly Leu Ser Lys Leu Asn Leu Met Ala Ala Ser Ala Gly Val
275                 280                 285                 290 gcg ccc gct ggc ttc tct tac tgg cct ggt ccc aac gcc acc gcc gct     1029
Ala Pro Ala Gly Phe Ser Tyr Trp Pro Gly Pro Asn Ala Thr Ala Ala
                295                 300                 305 gcc gcc gcc acc gct gcg ctc tac cca acc ccg ggc ttg cag ccc cct     1077
Ala Ala Ala Thr Ala Ala Leu Tyr Pro Thr Pro Gly Leu Gln Pro Pro
            310                 315                 320 ccc ggg ccc ttt ggc gcg gtg gcc gcc gct tcg cac ttg ggg ggt cat     1125
Pro Gly Pro Phe Gly Ala Val Ala Ala Ala Ser His Leu Gly Gly His
        325                 330                 335 tat cac tagacgggac ggccgggtgc agtggggcct ctcccacaca gccagtgacc     1181
Tyr His
    340 aatcccatcc tcatcctggg aggagccccg aagatttccc cgacgttcct ttaccacaga   1241 tttcgttgca gcagccgctc ccagcccagg gaagaaagga tgggaagcct ctgaggtctt   1301 ccttgaatac gaggcttcca ggctcccatt atcatcaccc caggaagggt gcatgtgctc   1361 ccactttaat ttttctcttc caagtctcca gattctggaa ctcccgtctt ttttttctct   1421 tctcacctgg agccctgcc ttcctcttta tgacccctag ttttctgttt tgttttttt    1481 ttttcctctc tctctcctca ttttttttct ctcccacgac ctactccaaa cggtagtacc   1541 tcggtagtac ctcgaggctt ctcacactcc ccttttcggg atatgagaag catcaaaaac   1601 atctctgctg ttgtccatcc ctatcccaac actctggctt cgctcccttc cataccacac   1661 tctggcccaa ggaccctcgt ctgtatatat tcctttcagc cccattaaag atccaagctt   1721 caaaaaaaaa aaaaaaaaaa aaaaaaaaaa a                                  1752

<210> SEQ ID NO 2
<211> LENGTH: 340
<212> TYPE: PRT
<213> ORGANISM: Rattus norvegicus

<400> SEQUENCE: 2

Met Glu Asp Pro Gly Gly Ala Pro Leu Gly Glu Arg Val Pro Ala Pro
1               5                   10                  15

His Pro Pro Gln Pro His Pro Leu Thr Ala His Ser Ser Ser Thr Pro
            20                  25                  30

Ala Pro Gly Trp Ala Gly Met Gln Leu Gln Asp Pro Leu Pro Pro His
        35                  40                  45

His Thr Leu Ala Ala Arg Ser Arg Gln Ala Leu Pro Asp Pro Ala Ala
    50                  55                  60

Ser Thr Leu Pro Cys His Pro Gln Ser Pro Arg Ala Gly Ile Gly Thr
65                  70                  75                  80

Pro Ser Ala Lys Leu Thr Cys Pro Pro Val Arg Ser Pro Ser Pro
            85                  90                  95

Thr Ala Gln Ser Pro Ala Ala Met Arg Gln Ser Gly Thr Ser Gln Pro
            100                 105                 110

Leu Leu Ile Asn Met Tyr Leu Pro Asp Pro Val Gly Asp Gly Leu Phe
        115                 120                 125

Lys Glu Gly Lys Ser Pro Ser Trp Gly Pro Leu Ser Pro Ala Val Gln
    130                 135                 140
```

```
Lys Gly Ser Gly Gln Ile Gln Leu Trp Gln Phe Leu Glu Leu Leu
145                 150                 155                 160

Ala Asp Arg Ala Asn Ala Gly Cys Ile Ala Trp Glu Gly Gly His Gly
            165                 170                 175

Glu Phe Lys Leu Thr Asp Pro Asp Glu Val Ala Arg Arg Trp Gly Glu
            180                 185                 190

Arg Lys Ser Lys Pro Asn Met Asn Tyr Asp Lys Leu Ser Arg Ala Leu
            195                 200                 205

Arg Tyr Tyr Tyr Asp Lys Asn Ile Met Ser Lys Val His Gly Lys Arg
    210                 215                 220

Tyr Ala Tyr Arg Phe Asp Phe Gln Gly Leu Ala Gln Ala Cys Gln Pro
225                 230                 235                 240

Pro Pro Ala His Ala His Ala Ala Ala Ala Ala Ala Ala Ala Ala Ala
                245                 250                 255

Ala Ala Gln Asp Gly Ala Leu Tyr Lys Leu Pro Ala Gly Leu Ala Pro
            260                 265                 270

Leu Pro Phe Pro Gly Leu Ser Lys Leu Asn Leu Met Ala Ala Ser Ala
            275                 280                 285

Gly Val Ala Pro Ala Gly Phe Ser Tyr Trp Pro Gly Pro Asn Ala Thr
    290                 295                 300

Ala Ala Ala Ala Ala Thr Ala Ala Leu Tyr Pro Thr Pro Gly Leu Gln
305                 310                 315                 320

Pro Pro Pro Gly Pro Phe Gly Ala Val Ala Ala Ala Ser His Leu Gly
                325                 330                 335

Gly His Tyr His
            340
```

<210> SEQ ID NO 3
<211> LENGTH: 11
<212> TYPE: DNA
<213> ORGANISM: Polyomavirus enhancer

<400> SEQUENCE: 3
agcaggaagt g                                                    11

<210> SEQ ID NO 4
<211> LENGTH: 11
<212> TYPE: DNA
<213> ORGANISM: Homo sapiens

<400> SEQUENCE: 4
agcaggaagt t                                                    11

<210> SEQ ID NO 5
<211> LENGTH: 11
<212> TYPE: DNA
<213> ORGANISM: Mus musculus

<400> SEQUENCE: 5
agcgggaagt t                                                    11

<210> SEQ ID NO 6
<211> LENGTH: 11
<212> TYPE: DNA
<213> ORGANISM: Homo sapiens

<400> SEQUENCE: 6
gaaaggaaat a                                                    11

```
<210> SEQ ID NO 7
<211> LENGTH: 11
<212> TYPE: DNA
<213> ORGANISM: Homo sapiens

<400> SEQUENCE: 7
gataggaagt a                                                          11

<210> SEQ ID NO 8
<211> LENGTH: 11
<212> TYPE: DNA
<213> ORGANISM: Mus musculus

<400> SEQUENCE: 8
cccaggaaat g                                                          11

<210> SEQ ID NO 9
<211> LENGTH: 11
<212> TYPE: DNA
<213> ORGANISM: Mus musculus

<400> SEQUENCE: 9
gggaggaaat g                                                          11

<210> SEQ ID NO 10
<211> LENGTH: 11
<212> TYPE: DNA
<213> ORGANISM: Homo sapiens

<400> SEQUENCE: 10
atacggaaat t                                                          11

<210> SEQ ID NO 11
<211> LENGTH: 11
<212> TYPE: DNA
<213> ORGANISM: Mus musculus

<400> SEQUENCE: 11
tacaggatat a                                                          11

<210> SEQ ID NO 12
<211> LENGTH: 11
<212> TYPE: DNA
<213> ORGANISM: Rattus norvegicus

<400> SEQUENCE: 12
ttcaggaaat t                                                          11

<210> SEQ ID NO 13
<211> LENGTH: 7
<212> TYPE: PRT
<213> ORGANISM: Artificial Sequence
<220> FEATURE:
<221> NAME/KEY: SITE
<222> LOCATION: (1)
<223> OTHER INFORMATION: The amino acid at this position can be
      isoleucine, valine, or leucine.
<220> FEATURE:
<221> NAME/KEY: SITE
<222> LOCATION: (2)
<223> OTHER INFORMATION: The amino acid at this position can be
      glutamine, tyrosine, or threonine.
<220> FEATURE:
<221> NAME/KEY: SITE
<222> LOCATION: (5)
<223> OTHER INFORMATION: The amino acid at this position can be glutamic
```

```
       acid or glutamine.
<220> FEATURE:
<223> OTHER INFORMATION: Description of Artificial Sequence:  Synthetic

<400> SEQUENCE: 13

Xaa Xaa Leu Trp Xaa Phe Leu
 1               5

<210> SEQ ID NO 14
<211> LENGTH: 7
<212> TYPE: PRT
<213> ORGANISM: Artificial Sequence
<220> FEATURE:
<221> NAME/KEY: SITE
<222> LOCATION: (4)
<223> OTHER INFORMATION: The amino acid at this position can be aspartic
       acid or glutamic acid.
<220> FEATURE:
<221> NAME/KEY: SITE
<222> LOCATION: (5)
<223> OTHER INFORMATION: The amino acid at this position can be lysine
       or threonine.
<220> FEATURE:
<221> NAME/KEY: SITE
<222> LOCATION: (6)
<223> OTHER INFORMATION: The amino acid at this position can be leucine
       or methionine.
<220> FEATURE:
<221> NAME/KEY: SITE
<222> LOCATION: (7)
<223> OTHER INFORMATION: The amino acid at this position can be serine
       or glycine.
<220> FEATURE:
<223> OTHER INFORMATION: Description of Artificial Sequence:  Synthetic

<400> SEQUENCE: 14

Met Asn Tyr Xaa Xaa Xaa Xaa
 1               5

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:  Synthetic

<400> SEQUENCE: 15
gcctctagak rtkhmkytkt ggsagtttyt                                      30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:  Synthetic

<400> SEQUENCE: 16
cccggtacck kshkaktktk tcgtagttca t                                    31

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:  Synthetic

<400> SEQUENCE: 17

Glu Glu Glu Glu Tyr Met Pro Met Glu
 1               5
```

```
<210> SEQ ID NO 18
<211> LENGTH: 15
<212> TYPE: DNA
<213> ORGANISM: Polyomarvirus enhancer
<220> FEATURE:
<223> OTHER INFORMATION: Description of Artificial Sequence:  Synthetic

<400> SEQUENCE: 18
gatccaggaa gtgac                                                        15

<210> SEQ ID NO 19
<211> LENGTH: 15
<212> TYPE: DNA
<213> ORGANISM: Polyomarvirus enhancer

<400> SEQUENCE: 19
gtcacttcct ggatc                                                        15

<210> SEQ ID NO 20
<211> LENGTH: 15
<212> TYPE: DNA
<213> ORGANISM: Polyomarvirus enhancer

<400> SEQUENCE: 20
gatccatcaa gtgac                                                        15

<210> SEQ ID NO 21
<211> LENGTH: 15
<212> TYPE: DNA
<213> ORGANISM: Polyomarvirus enhancer

<400> SEQUENCE: 21
gtcacttgat ggatc                                                        15

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence:  Synthetic

<400> SEQUENCE: 22
caggaagtga ctcaggaagt gactcaggaa gtgacac                                37

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:  Synthetic

<400> SEQUENCE: 23
catcaagtga ctcatcaagt gactcatcaa gtgacac                                37
```